US009326789B2

(12) United States Patent
Fruland et al.

(10) Patent No.: US 9,326,789 B2
(45) Date of Patent: May 3, 2016

(54) FLEXIBLE DEBULKING CATHETERS WITH IMAGING AND METHODS OF USE AND MANUFACTURE

(71) Applicant: Covidien LP, Mansfield, MA (US)

(72) Inventors: Benjamin Robert Fruland, Blaine, MN (US); Zachary Thomas Garvey, Stillwater, MN (US); Ethan Andrew Guggenheimer, Minneapolis, MN (US); Thomas John McPeak, Shakopee, MN (US); John Arthur Pedersen, Eden Prairie, MN (US); Scott Robert Petersen, Mansfield, MA (US); Lindsay Ann Crescenzo, Blaine, MN (US)

(73) Assignee: Covidien Lp, Mansfield, MA (US)

( * ) Notice: Subject to any disclaimer, the term of this patent is extended or adjusted under 35 U.S.C. 154(b) by 1 day.

(21) Appl. No.: 14/303,760

(22) Filed: Jun. 13, 2014

(65) Prior Publication Data

US 2015/0080700 A1     Mar. 19, 2015

Related U.S. Application Data

(63) Continuation of application No. 13/293,798, filed on Nov. 10, 2011, now Pat. No. 8,808,186.

(60) Provisional application No. 61/509,866, filed on Jul. 20, 2011, provisional application No. 61/412,674, filed on Nov. 11, 2010.

(51) Int. Cl.
*A61B 17/32* (2006.01)
*A61B 17/3207* (2006.01)
(Continued)

(52) U.S. Cl.
CPC ....... *A61B 17/320783* (2013.01); *A61B 5/0066* (2013.01); *A61B 5/0086* (2013.01);
(Continued)

(58) Field of Classification Search
CPC ........... A61B 17/320783; A61B 8/445; A61B 2017/003; A61B 2017/00526; A61M 2025/0681; A61M 25/01; A61M 25/0105; A61M 25/0138
USPC ........................ 600/459; 604/95.04, 264, 528
See application file for complete search history.

(56) References Cited

U.S. PATENT DOCUMENTS

| 1,481,078 A | 1/1924 | Albertson |
| 2,178,790 A | 11/1939 | Henry |

(Continued)

FOREIGN PATENT DOCUMENTS

| CA | 2000621 | 4/1990 |
| DE | 3732236 C1 | 12/1988 |

(Continued)

OTHER PUBLICATIONS

Notice of Reasons for Rejection with English translation for Japanese Application No. 2013-538892, dated Apr. 23, 2014, 7 pages.
(Continued)

*Primary Examiner* — Gerald Landry, II

(57) ABSTRACT

Catheters and methods for removing material from (or "debulking") a body lumen while imaging the region comprised of the material are provided. The catheters can be used in body lumens, including but not limited to intravascular lumens such as coronary or peripheral arteries. The catheters include housings or other structures to mount or protect an imaging transducer. Generally, debulking catheters include a proximal portion, a distal portion having an opening, a cutting element which may be exposed through the opening to contact material in a body lumen and an imaging transducer with associated circuitry and display. The catheter debulks a body lumen when it is moved while the cutting element is in contact with the material in the lumen and the region comprised of the material is imaged before, after, or during catheter movement.

28 Claims, 26 Drawing Sheets

(51) Int. Cl.
*A61B 5/00* (2006.01)
*A61B 5/055* (2006.01)
*A61B 8/08* (2006.01)
*A61B 8/12* (2006.01)
*A61B 8/00* (2006.01)
*A61B 10/04* (2006.01)
*G01R 33/28* (2006.01)
*A61B 19/00* (2006.01)
*A61M 25/00* (2006.01)
*A61M 25/01* (2006.01)
*A61M 25/06* (2006.01)
*G10K 11/00* (2006.01)
*A61B 17/00* (2006.01)

(52) U.S. Cl.
CPC .............. *A61B 5/055* (2013.01); *A61B 5/6852* (2013.01); *A61B 8/0891* (2013.01); *A61B 8/12* (2013.01); *A61B 8/4209* (2013.01); *A61B 8/4281* (2013.01); *A61B 8/445* (2013.01); *A61B 8/4461* (2013.01); *A61B 10/04* (2013.01); *A61B 17/32002* (2013.01); *A61B 17/320758* (2013.01); *A61B 8/4472* (2013.01); *A61B 2017/00526* (2013.01); *A61B 2017/320791* (2013.01); *A61B 2019/528* (2013.01); *A61M 25/0082* (2013.01); *A61M 25/01* (2013.01); *A61M 25/0136* (2013.01); *A61M 2025/0096* (2013.01); *A61M 2025/0681* (2013.01); *G01R 33/287* (2013.01); *G10K 11/004* (2013.01); *Y10T 29/49826* (2015.01)

(56) References Cited

U.S. PATENT DOCUMENTS

| | | |
|---|---|---|
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Willson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |

(56) References Cited

U.S. PATENT DOCUMENTS

| | | | |
|---|---|---|---|
| 5,047,040 | A | 9/1991 | Simpson et al. |
| 5,049,124 | A | 9/1991 | Bales, Jr. |
| 5,053,044 | A | 10/1991 | Mueller et al. |
| 5,054,492 | A | 10/1991 | Scribner et al. |
| 5,064,435 | A | 11/1991 | Porter |
| 5,071,425 | A | 12/1991 | Gifford et al. |
| 5,074,841 | A | 12/1991 | Ademovic et al. |
| 5,077,506 | A | 12/1991 | Krause et al. |
| 5,078,722 | A | 1/1992 | Stevens |
| 5,078,723 | A | 1/1992 | Dance et al. |
| 5,084,010 | A | 1/1992 | Plaia et al. |
| 5,085,662 | A | 2/1992 | Willard |
| 5,087,265 | A | 2/1992 | Summers |
| 5,092,839 | A | 3/1992 | Kipperman |
| 5,092,873 | A | 3/1992 | Simpson et al. |
| 5,095,911 | A | 3/1992 | Pomeranz |
| 5,100,423 | A | 3/1992 | Fearnot |
| 5,100,424 | A | 3/1992 | Jang et al. |
| 5,100,426 | A | 3/1992 | Nixon |
| 5,110,822 | A | 5/1992 | Sherba et al. |
| 5,112,345 | A | 5/1992 | Farr |
| 5,114,399 | A | 5/1992 | Kovalcheck |
| 5,115,814 | A | 5/1992 | Griffith et al. |
| 5,120,323 | A | 6/1992 | Shockey et al. |
| 5,127,902 | A | 7/1992 | Fischell |
| 5,127,917 | A | 7/1992 | Niederhauser et al. |
| 5,135,531 | A | 8/1992 | Shiber |
| 5,154,705 | A | 10/1992 | Fleischhacker et al. |
| 5,154,724 | A | 10/1992 | Andrews |
| 5,165,421 | A | 11/1992 | Fleischhacker et al. |
| 5,176,693 | A | 1/1993 | Pannek, Jr. |
| 5,178,625 | A | 1/1993 | Groshong |
| 5,181,920 | A | 1/1993 | Mueller et al. |
| 5,183,432 | A | 2/1993 | Noguchi |
| 5,190,528 | A | 3/1993 | Fonger et al. |
| 5,192,291 | A | 3/1993 | Pannek, Jr. |
| 5,195,956 | A | 3/1993 | Stockmeier |
| 5,211,651 | A | 5/1993 | Reger et al. |
| 5,217,474 | A | 6/1993 | Zacca et al. |
| 5,222,966 | A | 6/1993 | Perkins et al. |
| 5,224,488 | A | 7/1993 | Neuffer |
| 5,224,945 | A | 7/1993 | Pannek, Jr. |
| 5,224,949 | A | 7/1993 | Gomringer et al. |
| 5,226,909 | A | 7/1993 | Evans et al. |
| 5,226,910 | A | 7/1993 | Kajiyama et al. |
| 5,234,451 | A | 8/1993 | Osypka |
| 5,242,460 | A | 9/1993 | Klein et al. |
| 5,242,461 | A | 9/1993 | Kortenbach et al. |
| 5,250,059 | A | 10/1993 | Andreas et al. |
| 5,250,065 | A | 10/1993 | Clement et al. |
| 5,263,928 | A | 11/1993 | Trauthen et al. |
| 5,263,959 | A | 11/1993 | Fischell |
| 5,267,955 | A | 12/1993 | Hanson |
| 5,267,982 | A | 12/1993 | Sylvanowicz |
| 5,269,793 | A | 12/1993 | Simpson et al. |
| 5,273,526 | A | 12/1993 | Dance et al. |
| 5,282,484 | A | 2/1994 | Reger |
| 5,284,486 | A | 2/1994 | Kotula et al. |
| 5,285,795 | A | 2/1994 | Ryan et al. |
| 5,295,493 | A | 3/1994 | Radisch, Jr. |
| 5,300,085 | A | 4/1994 | Yock |
| 5,306,294 | A | 4/1994 | Winston et al. |
| 5,308,354 | A | 5/1994 | Zacca et al. |
| 5,312,425 | A | 5/1994 | Evans et al. |
| 5,312,427 | A | 5/1994 | Shturman |
| 5,314,438 | A | 5/1994 | Shturman |
| 5,318,032 | A | 6/1994 | Lonsbury et al. |
| 5,318,528 | A | 6/1994 | Heaven et al. |
| 5,318,576 | A | 6/1994 | Plassche, Jr. et al. |
| 5,321,501 | A | 6/1994 | Swanson et al. |
| 5,322,508 | A | 6/1994 | Viera |
| 5,350,390 | A | 9/1994 | Sher |
| 5,356,418 | A | 10/1994 | Shturman |
| 5,358,472 | A | 10/1994 | Vance et al. |
| 5,358,485 | A | 10/1994 | Vance et al. |
| 5,360,432 | A | 11/1994 | Shturman |
| 5,366,463 | A | 11/1994 | Ryan |
| 5,368,035 | A | 11/1994 | Hamm et al. |
| 5,370,609 | A | 12/1994 | Drasler et al. |
| 5,370,651 | A | 12/1994 | Summers |
| 5,372,601 | A | 12/1994 | Lary |
| 5,372,602 | A | 12/1994 | Burke |
| 5,373,619 | A | 12/1994 | Fleischhacker et al. |
| 5,373,849 | A | 12/1994 | Maroney et al. |
| 5,377,682 | A | 1/1995 | Ueno et al. |
| 5,378,234 | A | 1/1995 | Hammerslag et al. |
| 5,383,460 | A | 1/1995 | Jang et al. |
| 5,395,311 | A | 3/1995 | Andrews |
| 5,395,313 | A | 3/1995 | Naves et al. |
| 5,395,335 | A | 3/1995 | Jang |
| 5,397,345 | A | 3/1995 | Lazarus |
| 5,400,785 | A | 3/1995 | Crowley |
| 5,402,790 | A | 4/1995 | Jang et al. |
| 5,403,334 | A | 4/1995 | Evans et al. |
| 5,409,454 | A | 4/1995 | Fischell et al. |
| 5,413,107 | A | 5/1995 | Oakley et al. |
| 5,419,774 | A | 5/1995 | Willard et al. |
| 5,423,740 | A | 6/1995 | Sullivan et al. |
| 5,423,799 | A | 6/1995 | Shiu |
| 5,423,838 | A | 6/1995 | Willard |
| 5,423,846 | A | 6/1995 | Fischell |
| 5,427,107 | A | 6/1995 | Milo et al. |
| 5,429,136 | A | 7/1995 | Milo et al. |
| 5,431,673 | A | 7/1995 | Summers et al. |
| 5,441,510 | A | 8/1995 | Simpson et al. |
| 5,443,446 | A | 8/1995 | Shturman |
| 5,443,497 | A | 8/1995 | Venbrux |
| 5,444,078 | A | 8/1995 | Yu et al. |
| 5,445,155 | A | 8/1995 | Sieben |
| 5,449,369 | A | 9/1995 | Imran |
| 5,451,233 | A | 9/1995 | Yock |
| 5,454,809 | A | 10/1995 | Janssen |
| 5,456,667 | A | 10/1995 | Ham et al. |
| 5,456,689 | A | 10/1995 | Kresch et al. |
| 5,458,585 | A | 10/1995 | Salmon et al. |
| 5,459,570 | A | 10/1995 | Swanson et al. |
| 5,464,016 | A | 11/1995 | Nicholas et al. |
| 5,470,415 | A | 11/1995 | Perkins et al. |
| 5,485,042 | A | 1/1996 | Burke et al. |
| 5,485,840 | A | 1/1996 | Bauman |
| 5,487,729 | A | 1/1996 | Avellanet et al. |
| 5,489,295 | A | 2/1996 | Piplani et al. |
| 5,491,524 | A | 2/1996 | Hellmuth et al. |
| 5,496,267 | A | 3/1996 | Drasler et al. |
| 5,501,694 | A | 3/1996 | Ressemann et al. |
| 5,503,155 | A | 4/1996 | Salmon et al. |
| 5,505,210 | A | 4/1996 | Clement |
| 5,507,292 | A | 4/1996 | Jang et al. |
| 5,507,760 | A | 4/1996 | Wynne et al. |
| 5,507,761 | A | 4/1996 | Duer |
| 5,507,795 | A | 4/1996 | Chiang et al. |
| 5,512,044 | A | 4/1996 | Duer |
| 5,514,115 | A | 5/1996 | Frantzen et al. |
| 5,520,189 | A | 5/1996 | Malinowski et al. |
| 5,522,825 | A | 6/1996 | Kropf et al. |
| 5,522,880 | A | 6/1996 | Barone et al. |
| 5,527,292 | A | 6/1996 | Adams et al. |
| 5,527,298 | A | 6/1996 | Vance et al. |
| 5,527,325 | A | 6/1996 | Conley et al. |
| 5,531,685 | A | 7/1996 | Hemmer et al. |
| 5,531,690 | A | 7/1996 | Solar |
| 5,531,700 | A | 7/1996 | Moore et al. |
| 5,540,707 | A | 7/1996 | Ressemann et al. |
| 5,549,601 | A | 8/1996 | McIntyre et al. |
| 5,554,163 | A | 9/1996 | Shturman |
| 5,556,408 | A | 9/1996 | Farhat |
| 5,558,093 | A | 9/1996 | Pomeranz |
| 5,562,726 | A | 10/1996 | Chuter |
| 5,562,728 | A | 10/1996 | Lazarus et al. |
| 5,569,275 | A | 10/1996 | Kotula et al. |
| 5,569,276 | A | 10/1996 | Jang et al. |
| 5,569,277 | A | 10/1996 | Evans et al. |
| 5,569,279 | A | 10/1996 | Rainin |
| 5,570,693 | A | 11/1996 | Jang et al. |

(56) References Cited

U.S. PATENT DOCUMENTS

| | | |
|---|---|---|
| 5,571,122 A | 11/1996 | Kelly et al. |
| 5,571,130 A | 11/1996 | Simpson et al. |
| 5,575,817 A | 11/1996 | Martin |
| 5,582,178 A | 12/1996 | Yock |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike et al. |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wilson et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A * | 3/2000 | Spaulding .................. 606/159 |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |

(56) References Cited

U.S. PATENT DOCUMENTS

| | | |
|---|---|---|
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 * | 10/2001 | Snow ............... A61B 17/32075 606/159 |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antonaides et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 * | 8/2010 | Patel et al. ............ 606/159 |
| 7,887,556 B2 | 2/2011 | Simpson et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 * | 6/2002 | Patel et al. ............ 606/167 |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 * | 7/2003 | Patel et al. ............ 606/159 |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 * | 10/2005 | Simpson et al. ............ 623/1.11 |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |

(56) References Cited

U.S. PATENT DOCUMENTS

| | | | |
|---|---|---|---|
| 2007/0265647 A1 | 11/2007 | Bonnette et al. | |
| 2007/0276419 A1* | 11/2007 | Rosenthal | 606/159 |
| 2008/0001643 A1 | 1/2008 | Lee | |
| 2008/0004644 A1 | 1/2008 | To et al. | |
| 2008/0004645 A1 | 1/2008 | To et al. | |
| 2008/0004646 A1 | 1/2008 | To et al. | |
| 2008/0004647 A1 | 1/2008 | To et al. | |
| 2008/0045986 A1 | 2/2008 | To et al. | |
| 2008/0051812 A1 | 2/2008 | Schmitz et al. | |
| 2008/0065124 A1* | 3/2008 | Olson | A61B 17/320783 606/159 |
| 2008/0065125 A1* | 3/2008 | Olson | A61B 17/320758 606/159 |
| 2008/0097403 A1* | 4/2008 | Donaldson et al. | 604/528 |
| 2008/0125799 A1 | 5/2008 | Adams | |
| 2008/0161840 A1 | 7/2008 | Osiroff et al. | |
| 2008/0177139 A1 | 7/2008 | Courtney et al. | |
| 2008/0208227 A1 | 8/2008 | Kadykowski et al. | |
| 2008/0249553 A1 | 10/2008 | Gruber et al. | |
| 2008/0312673 A1 | 12/2008 | Viswanathan et al. | |
| 2009/0012548 A1 | 1/2009 | Thatcher et al. | |
| 2009/0018565 A1 | 1/2009 | To et al. | |
| 2009/0018566 A1 | 1/2009 | Escudero et al. | |
| 2009/0018567 A1* | 1/2009 | Escudero et al. | 606/159 |
| 2009/0024085 A1* | 1/2009 | To et al. | 604/95.01 |
| 2009/0138031 A1 | 5/2009 | Tsukernik | |
| 2009/0187203 A1 | 7/2009 | Corvi et al. | |
| 2009/0216125 A1 | 8/2009 | Lenker | |
| 2009/0216180 A1 | 8/2009 | Lee et al. | |
| 2009/0226063 A1 | 9/2009 | Rangwala et al. | |
| 2009/0234378 A1 | 9/2009 | Escudero et al. | |
| 2009/0270888 A1* | 10/2009 | Patel | A61B 17/320758 606/159 |
| 2009/0275966 A1 | 11/2009 | Mitusina | |
| 2009/0299394 A1 | 12/2009 | Simpson et al. | |
| 2009/0306689 A1 | 12/2009 | Welty et al. | |
| 2010/0030216 A1 | 2/2010 | Arcenio | |
| 2010/0049225 A1 | 2/2010 | To et al. | |
| 2010/0130996 A1 | 5/2010 | Doud et al. | |
| 2010/0198240 A1 | 8/2010 | Simpson et al. | |
| 2010/0241147 A1 | 9/2010 | Maschke | |
| 2010/0280316 A1* | 11/2010 | Dietz | A61B 8/12 600/109 |
| 2010/0280534 A1 | 11/2010 | Sher | |
| 2010/0292721 A1 | 11/2010 | Moberg | |
| 2010/0298850 A1 | 11/2010 | Snow et al. | |
| 2010/0312263 A1 | 12/2010 | Moberg et al. | |
| 2011/0004107 A1 | 1/2011 | Rosenthal et al. | |
| 2011/0022069 A1 | 1/2011 | Mitusina | |
| 2011/0040315 A1 | 2/2011 | To et al. | |
| 2011/0130777 A1 | 6/2011 | Zhang et al. | |
| 2011/0144673 A1 | 6/2011 | Zhang et al. | |
| 2011/0257042 A1* | 10/2011 | Simpson | 506/17 |
| 2012/0108979 A1* | 5/2012 | Franklin et al. | 600/463 |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | 9316642 A2 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | 9916356 A1 | 4/1999 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | 2006058223 A2 | 6/2006 |
| WO | 2006066012 | 6/2006 |

OTHER PUBLICATIONS

Brezinski et al., "Optical Coherence Tomography for Optical Biopsy," Circulation, 93:1206-1213 (1996).

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

Extended European Search Report for European Application No. 13174640.6, dated Apr. 2, 2014, 5 pages.

Patent Examination Report No. 1 for Australian Application No. 2011326420, Jul. 9, 2014, 4 pages.

Notification of the First Office Action with English translation for Chinese Application No. 201180062605.8, Jul. 16, 2014, 21 pages.

International Search Report and Written Opinion for PCT Application No. PCT/US2011/060203, dated May 14, 2013, 9 pages.

KIPO's Notice of Preliminary Rejection with English Translation for Application No. 10-2013-7014822, dated Oct. 2, 2014, 9 pages.

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

(56) References Cited

OTHER PUBLICATIONS

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (2 pages).

Office action for Canadian Application No. 2,817,213, dated Nov. 24, 2014, 5 pages.

Office action for Russian Application No. 2013122590/14 with English translation, dated Oct. 14, 2014, 11 pages.

* cited by examiner

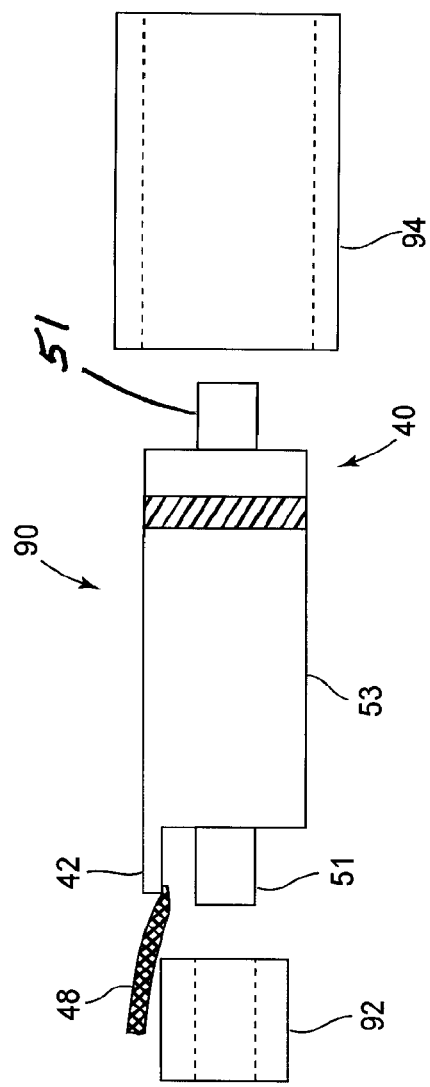
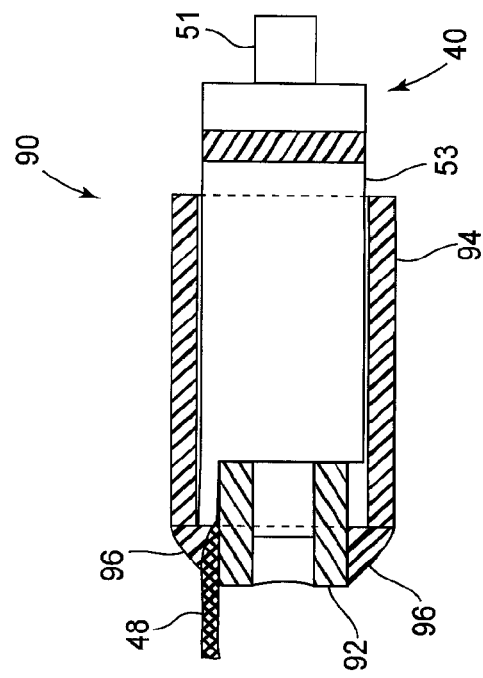
FIG. 9A
FIG. 9B

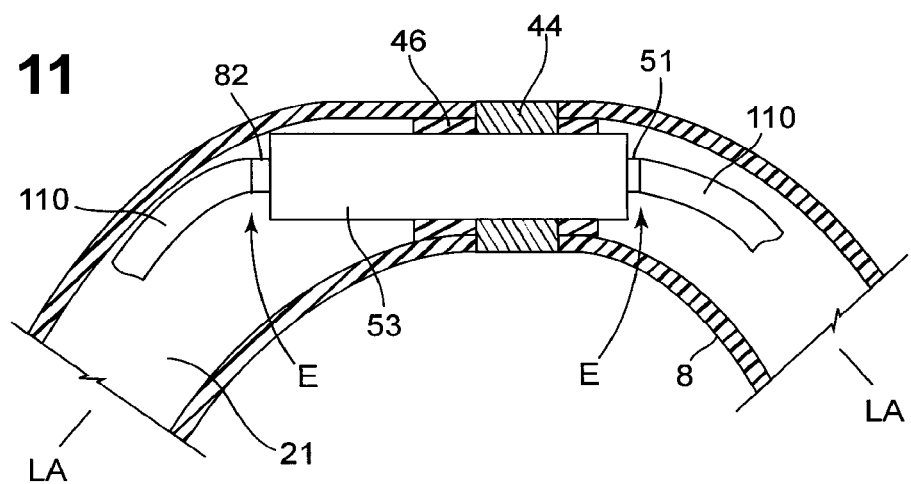

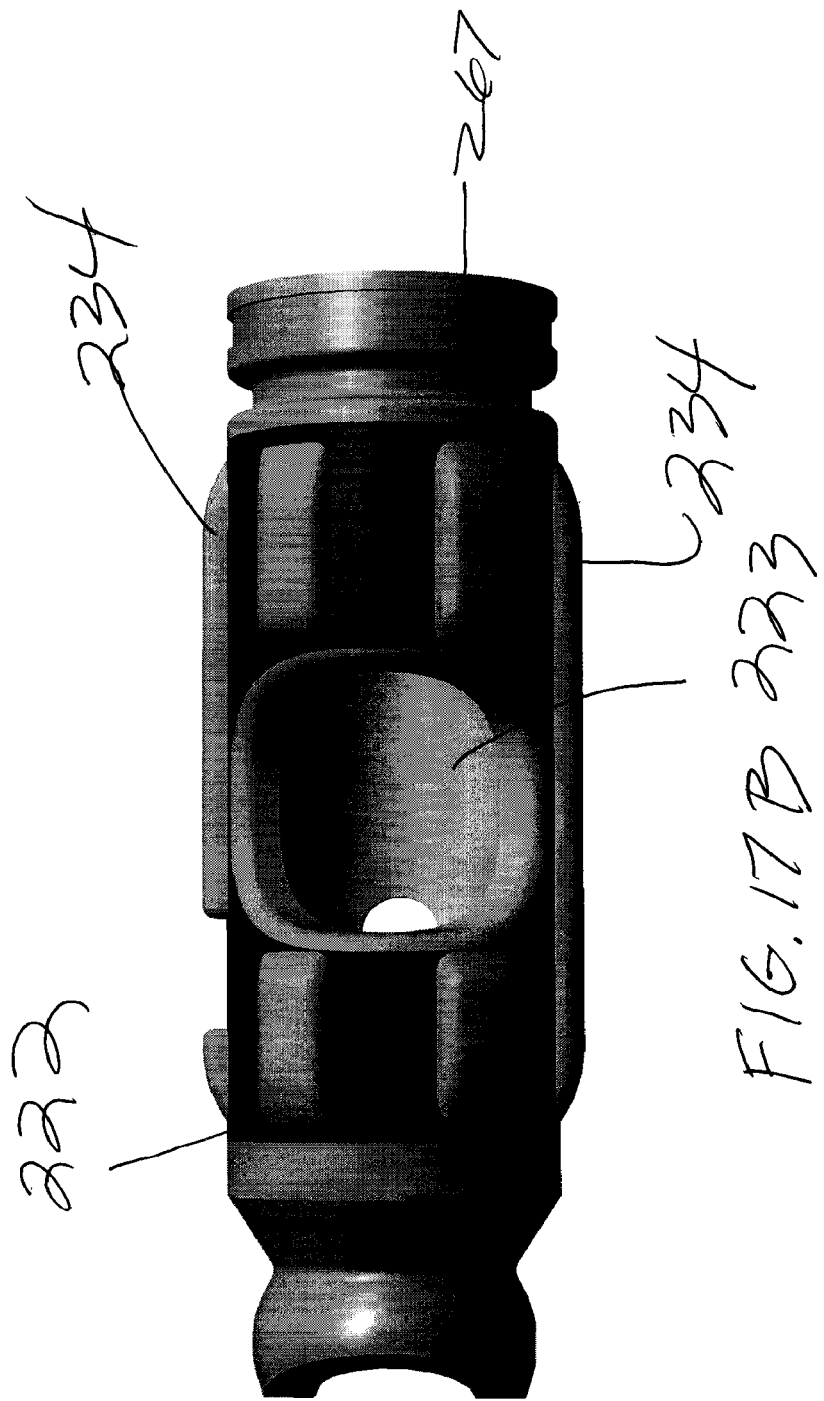

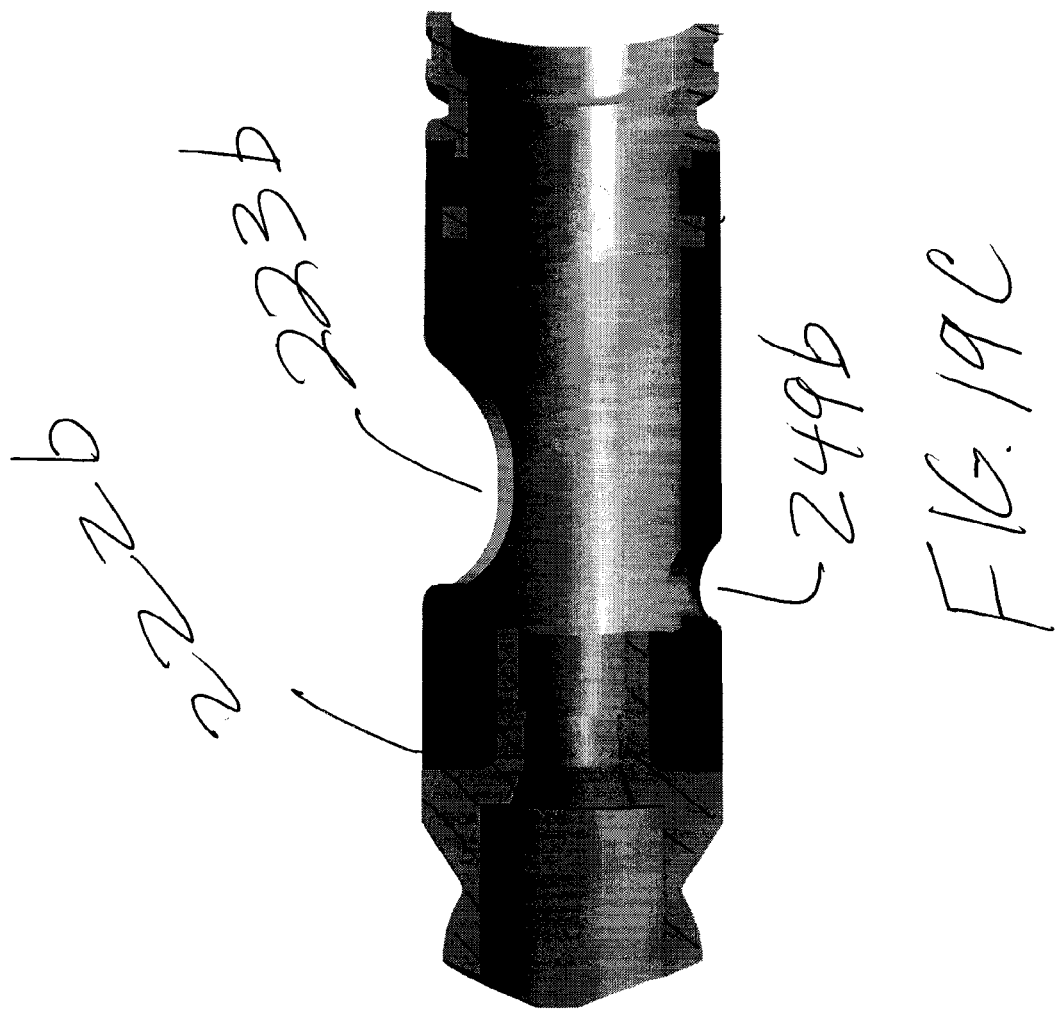

FLEXIBLE DEBULKING CATHETERS WITH IMAGING AND METHODS OF USE AND MANUFACTURE

CROSS-REFERENCE TO RELATED APPLICATION

This application is a continuation of U.S. application Ser. No. 13/293,798, filed Nov. 10, 2011, entitled "Flexible Debulking Catheters with Imaging and Methods of Use and Manufacture", which claims the benefit of U.S. Provisional Patent Application No. 61/509,866, filed Jul. 20, 2011, entitled "Flexible Debulking Catheters with Imaging and Methods of Use", and U.S. Provisional Patent Application No. 61/412,674, filed Nov. 11, 2010, entitled "Flexible Debulking Catheters with Imaging and Methods of Use", the contents of each of which are hereby incorporated by reference herein.

FIELD OF THE INVENTION

The present invention relates generally to systems and methods for debulking body lumens. More particularly, the present invention relates to atherectomy catheters for treating vascular disease.

BACKGROUND OF THE INVENTION

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease, and atherosclerosis in particular, can be treated in a variety of ways, including drugs, bypass surgery, and a variety of catheter-based approaches. One catheter based approach is intravascular debulking or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side and a blade which is rotated or translated past the aperture.

Although atherectomy catheters have been considered successful in treating many types of atherosclerosis and restenosis, improved atherectomy catheters and methods are continuously being pursued. For example, many currently available atherectomy catheters have cutters enclosed in relatively large diameter distal housings to assure that the cutter can be safely transported within the vessel. To provide storage capacity for sufficient volume of material while treating the vessel the cutter housings are often lengthened. It has also been proposed to combine imaging into atherectomy catheters. Imaging transducers, if provided, may impact the flexibility of the distal catheter region because the transducers are generally rigid. Decreased flexibility and increased length of the distal catheter region may make it more difficult to introduce and withdraw the distal end of the catheter through tortuous regions of the vasculature.

The present invention overcomes some of these problems associated with prior art devices. In particular, the present invention relates to methods and devices for imaging and removing tissue from a body lumen such as a blood vessel or other vascular location. Although the present invention may be used for removing material from a vascular location it may find uses in other body lumens as well. It is understood that although the invention may be described with respect to use in blood vessels the methods and devices of the present invention may be practiced in any body lumen.

SUMMARY OF THE INVENTION

Various catheter embodiments and their methods of use and manufacture are disclosed herein. Distinguishing features that may be included in these catheter embodiments and methods are described below in connection with specific embodiments or methods. It is intended that the catheters and methods described herein may include one or more of these features individually or in combination and it is not intended that this disclosure be limited to the specific combination of features described in connection with the embodiments or methods disclosed herein.

The embodiments disclosed herein are directed to catheters and methods for removing material from (or "debulking") a body lumen while imaging the lumen and to methods of making the catheters. These catheters have sufficient flexibility, torqueability and tensile strength to be used in a variety of body lumens, including but not limited to intravascular lumens such as coronary or peripheral vasculature. Debulking catheters are used to remove occlusive material, such as atherosclerotic plaque, from vascular lumens, but they may alternatively be used to remove other materials. Generally, debulking catheters include a proximal portion, a distal portion having an opening (or "window"), a cutting element (or "tissue debulking assembly") which may be exposed through the opening to contact material in a body lumen and an imaging transducer with associated circuitry and display. The catheter debulks a body lumen when it is moved while the cutting element is in contact with the material in the lumen and the lumen 15 is imaged before, after, or during catheter movement.

The embodiments disclosed herein include catheters having imaging transducers within housings. The housings are designed to protect the transducer and/or wires or wire connectors connected to the transducer from damage during use of the catheter yet allow for suitable imaging when the catheter is in use. These catheters may also be provided with other features which allow the transducer to be mounted within the catheter body in a manner that protects the transducer and/or wires or wire connectors connecting the transducer to a control handle but allows the catheter body to maintain desired flexibility and image quality. These features include the use of flexible fillers, hydrophilic materials, transmissive materials, potting materials, various adaptors and other protective structure which is attached to or associated with the transducer.

For a further understanding of the nature and advantages of the invention, reference should be made to the following description taken in conjunction with the accompanying drawings.

BRIEF DESCRIPTION OF THE DRAWINGS

FIGS. 9A and 9B are partial cross sectional side views of another embodiment of an adapter for use with a transducer.

FIG. 11 is a partial cross sectional side view of a transducer mounted into a catheter.

FIGS. 17A to 17D are side, top and cross-sectional views of a transducer housing of the catheter of FIGS. 16A to 16C.

FIG. 19A to 19D are side, top and cross-sectional views of a transducer housing of the catheter of FIGS. 16A to 16C.

DETAILED DESCRIPTION OF PREFERRED EMBODIMENTS

Figure 1:
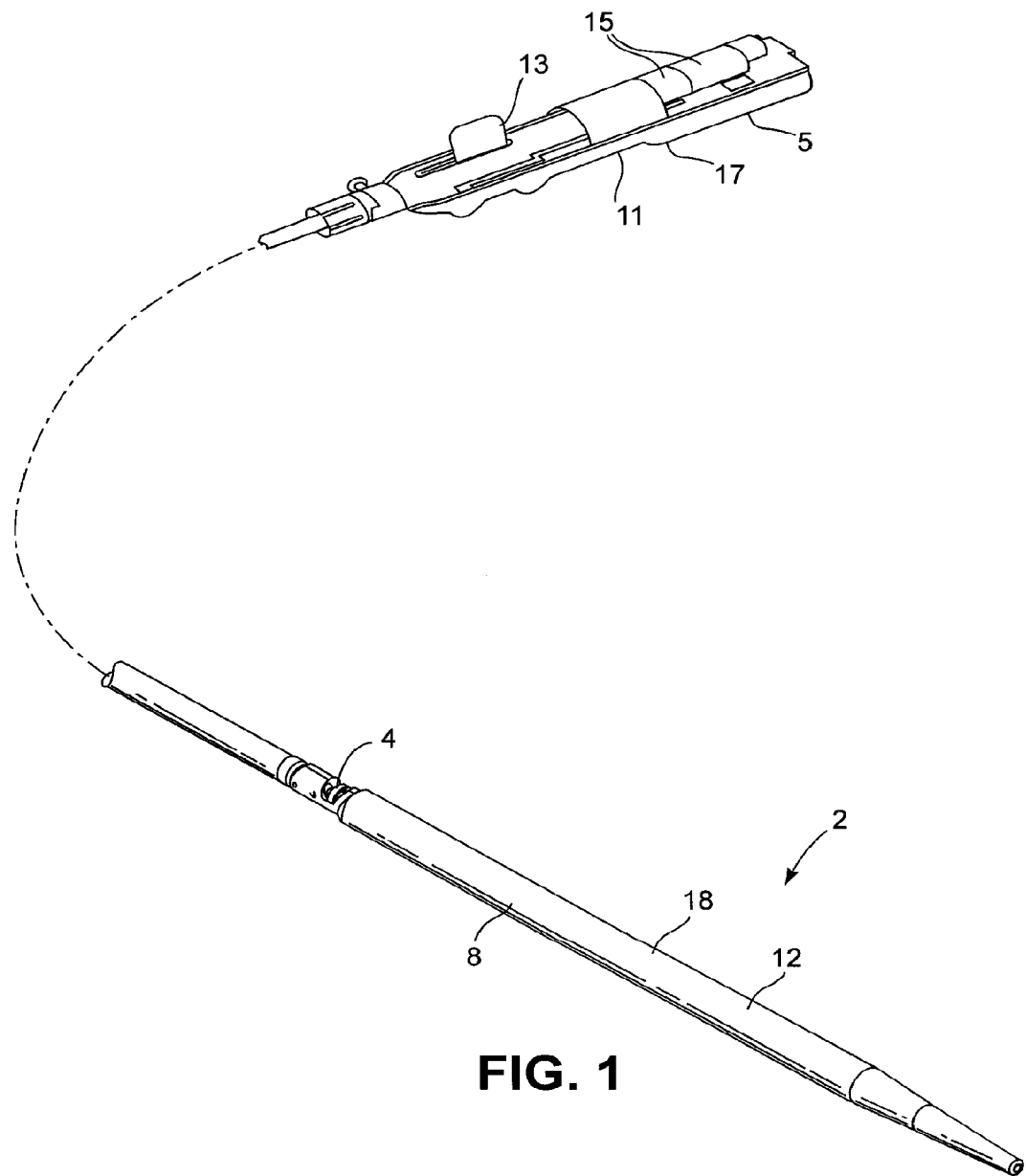
FIG. 1 is a partial isometric view of an atherectomy catheter.

The catheters and methods of the embodiments described herein are designed to debulk atheroma and other occlusive material from diseased body lumens, and in particular lesions in peripheral arteries. The catheters and methods are also suitable for treating stenoses of body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Debulking of such material can thus be beneficial to maintain patency of the body lumen. While the remaining discussion is directed at debulking and passing through atheromatous or thrombotic occlusive material in a peripheral artery, it will be appreciated that the systems and methods of the present invention can be used to remove and/or pass through a variety of occlusive, stenotic, or hyperplastic material in a variety of body lumens.

Apparatus according to the present invention will generally comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the distal portions of the catheter bodies will typically be very flexible and suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments.

The distal portion of the catheters described in these embodiments may have a wide variety of forms and structures. In many embodiments, a distal portion of the catheter is more flexible than a proximal portion, but in other embodiments the distal portion may be equally as flexible as the proximal portion or even more rigid than a proximal portion. One aspect of the present invention provides catheters having a distal portion with a reduced rigid length. The reduced rigid length can allow the catheters to access and treat tortuous vessels and small diameter body lumens. In most embodiments a rigid distal portion or housing of the catheter body will have a diameter that generally matches the proximal portion of the catheter body, however, in other embodiments, the distal portion may be larger or smaller than the flexible portion of the catheter. Additionally, many embodiments include a flexible distal tip.

The flexible proximal portion of the catheter is typically a torque shaft and the distal portion is typically rigid tubing. The torque shaft facilitates transportation of the catheter body and cutter to the diseased site. The proximal end of the torque shaft is coupled to a handle and the distal end of the torque shaft is attached to the distal, rigid portion of the catheter through the connection assembly. The drive shaft is movably positioned within the torque shaft so as to rotate and axially move within the torque shaft. The drive shaft and torque shaft are sized to allow relative movement of each shaft without interfering with the movement of the other shaft. The catheter body will have the pushability and torqueability such that torquing and pushing of the proximal end will translate motion to the distal portion of the catheter body.

The distal portion of the catheter body is comprised of a side opening window which may have a length of approximately 2 mm. In other embodiments, however, the side opening cutting window can be larger or smaller, but should be large enough to allow the cutter to protrude a predetermined distance that is sufficient to debulk material from the body lumen.

A rotatable cutter or other tissue debulking assembly may be disposed in the distal portion of the catheter to sever material which is adjacent to or received within the cutting window. In an exemplary embodiment, the cutter is movably disposed in the distal portion of the catheter body and movable across a side opening window. A straight or serrated cutting blade or other element can be formed integrally along a distal or proximal edge of the cutting window to assist in severing material from the body lumen. In one particular embodiment, the cutter has a diameter of approximately 1.75 mm. It should be appreciated however, that the diameter of the cutter will depend primarily on the diameter of the distal portion of the catheter body. The cutter is typically rotatable within the distal portion about an axis that is parallel to the longitudinal axis of the distal portion of the catheter and axially movable along the longitudinal axis.

By moving the cutter outside of the cutting window beyond an outer diameter of the distal portion of the catheter, the cutter is able to contact and sever material that does not invaginate through the cutting window. Moving the rotating cutter outside of the cutting window and advancing the entire catheter body distally, a large amount of occlusive material can be removed. Consequently, the amount of material that can be removed is not limited by the size of the cutting window.

A catheter constructed in accordance with principles of the present invention comprises a catheter body having a proximal portion and a distal portion. The proximal portion can be coupled to the distal portion with a connection assembly to allow pivoting or deflection of the distal portion relative to the proximal portion. In some embodiments disclosed herein a transducer housing is connected between the proximal and distal catheter portions. In these embodiments in addition to housing a transducer the housing functions as the connection assembly. A proximal end of the catheter body can have a handle for manipulation by a user, a luer port for connection to an aspiration or fluid delivery channel, or the like.

Catheters described in the embodiments disclosed herein additionally include vessel imaging capability and are used in conjunction with non-catheter based controls and one or more user interfaces. For example, an imaging transducer may be located on the catheter and connected to a non-catheter based control using one or more of wires, cables, connectors, wireless communication, or other means. Signal processing or signal conditioning components, either catheter based or non-catheter based, may be interspersed between the transducer and the control, or may be integrated on the transducer, the controller or any combination thereof. User interfaces may be comprised of visual displays, audible signals, tactile signals, or other means and can be catheter based, non-catheter based or both. Imaging transducers are catheter based and may transduce ultrasonic energy, light energy, infrared energy, magnetic energy, or combinations thereof. Some examples of known imaging modalities suitable for use in catheters of the present invention include intravascular ultrasound (IVUS), optical coherence tomography (OCT), and magnetic resonance imaging (MRI). While the remaining discussion is directed at IVUS, it will be appreciated that the catheters, systems and methods of the present invention can be comprised of any of IVUS, OCT or MRI imaging.

Referring to FIGS. 1 to 4, an atherectomy catheter 2 is shown which has a cutting element 4, which is used to cut material from a blood flow lumen. The cutting element 4 is movable between a stored position (FIG. 6) and a cutting or working position (FIG. 3) relative to a side opening 6 in a body 8 of the catheter 2. The cutting element 4 moves outwardly relative to the opening 6 so that a portion of the element 4 extends outwardly from the body 8 through the opening 6. The cutting element 4 may be positioned relative to the body 8 and opening 6 so that less than 90 degrees of the cutting element 4 is exposed to cut tissue. Of course, more of the cutting element 4 may be exposed without departing from numerous aspects of the invention.

Catheter 2 may have a size of 3, 4, 5, 6, 7, 8, 9, 10, or 12 French so that it is compatible with standard sheath sizes and, in particular, 6, 7 or 8 French sheath sizes. Catheter 2 may have a working length ranging from 20 to 210 cm, and more specifically, 100, 110, 113, 120, 133, 135, 136, 145, 150, 180, or 210 cm depending on the requirements of the anatomical location in which use of the catheter is contemplated. Cutter 4 preferably has a diameter slightly less than that of the maximum size of catheter 2, typically 0.010", 0.015", 0.20", 0.25" or 0.30" less. However, these relative dimensions are not meant to be limiting.

During the cutting procedure, the catheter 2 is moved through a vessel with the cutting element 4 in the working or cutting position as described in further detail below. As the catheter 2 moves through the lumen, the tissue is cut by the cutting element 4 and is directed into a tissue chamber 12 positioned distal to the cutting element 4. The tissue chamber 12 may be somewhat elongate to accommodate the tissue collected during operation of the catheter.

Figure 3:
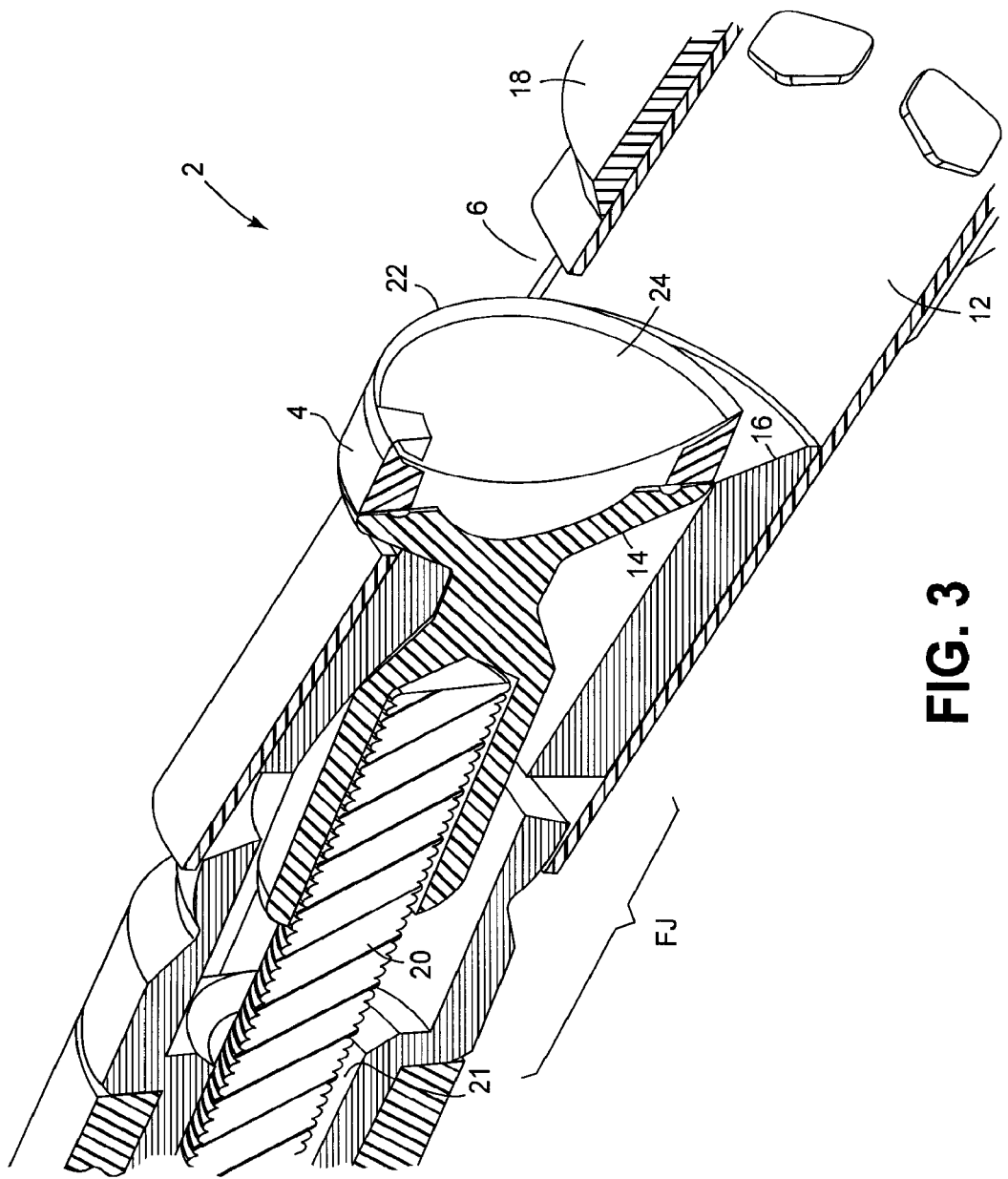
FIG. 3 is an isometric view of a portion of the atherectomy catheter of FIG. 1 with a cutting element in a working position.
Figure 4:
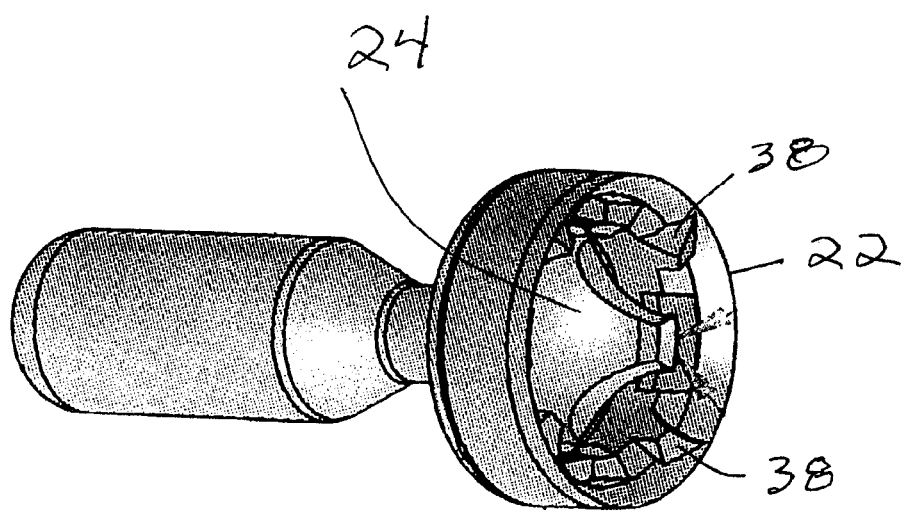
FIG. 4 is an isometric view of an embodiment of a cutting element.
Figure 6:
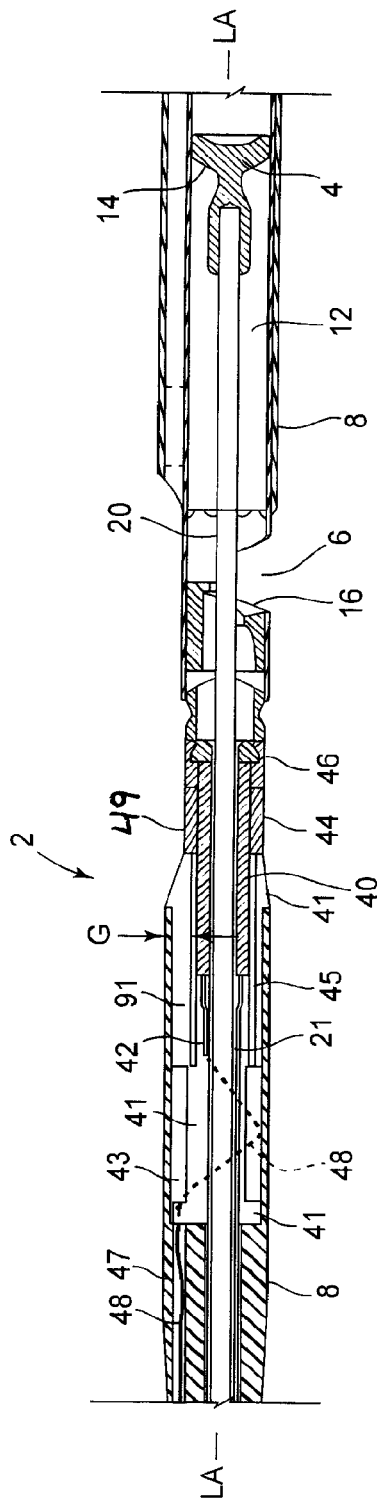
FIG. 6 is a partial cross-sectional view of a portion of the atherectomy catheter of FIG. 5 with a cutting element in a stored position.

The cutting element 4 is moved proximally from the stored position, shown in FIG. 6, so that a cam surface 14 on the cutting element 4 engages a ramp 16 on the body 8 of the catheter 2, as shown in FIG. 3. The interaction between the cam surface 14 and the ramp 16 causes the cutting element 4 to move to the cutting position and also causes a distal tip 18 of the catheter 2 to deflect which tends to move the cutting element 4 toward the tissue to be cut. Cutting element 4 may have one or more raised elements 38 on cup shaped surface 24 and a sharpened outermost edge 22.

Figure 2:
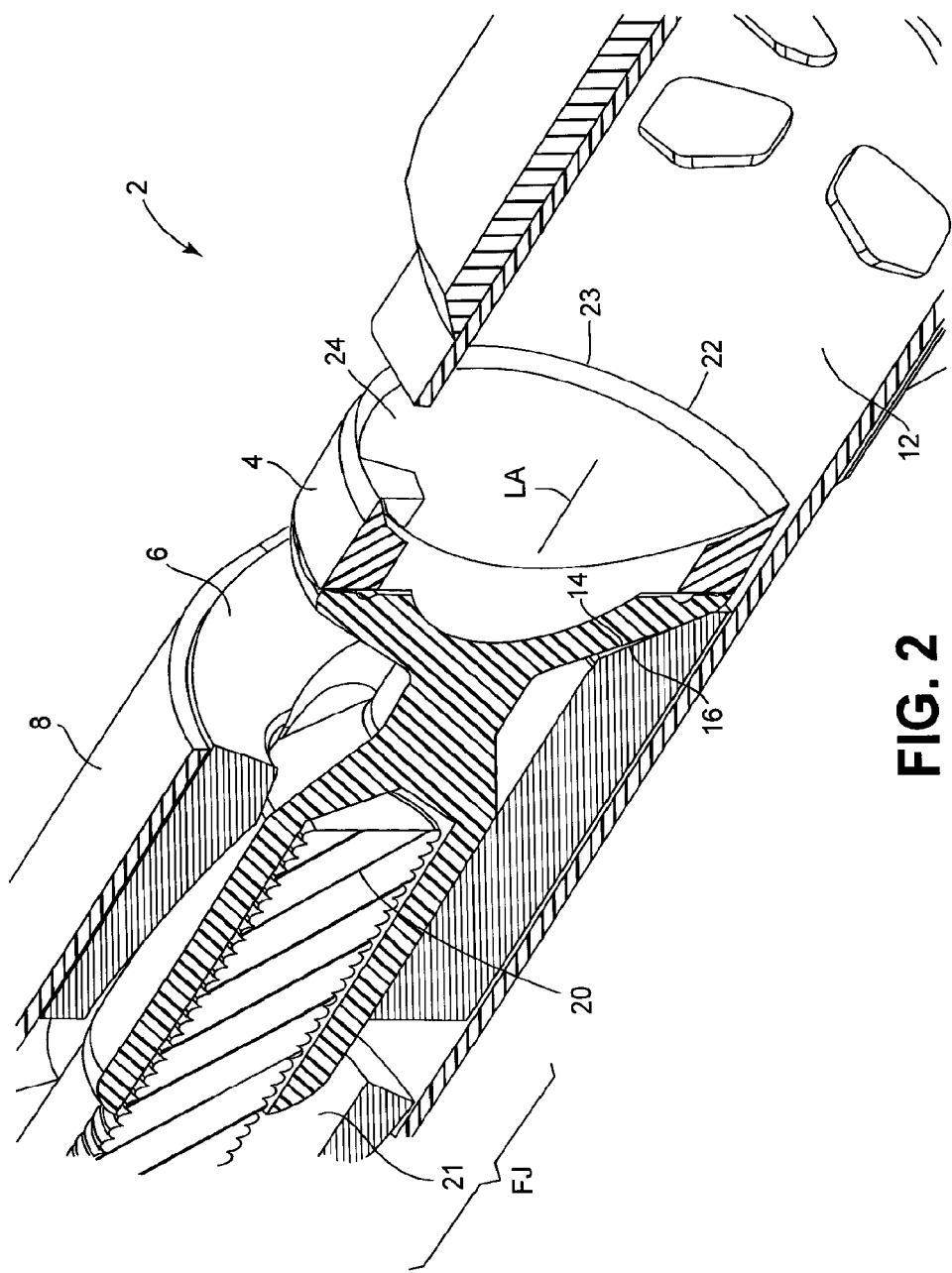
FIG. 2 is an isometric cross-sectional view of a portion of the atherectomy catheter of FIG. 1 with a cutting element shown partially exposed.

As shown in FIG. 2, the cutting element is coupled to a shaft 20 that extends through a lumen 21 in the catheter 2. Catheter 2 is coupled to exemplary cutter driver 5 shown in FIG. 1. Cutter driver 5 is comprised of motor 11, power source 15 (for example one or more batteries), a microswitch (not shown), housing 17 (upper half of housing is removed as shown), lever 13 and connection assembly (not shown) for connecting shaft 20 to driver motor 11. Cutter driver 5 can act as a handle for the user to manipulate catheter 2. Lever 13, when actuated to close the microswitch, electrically connects power source 15 to motor 11 thereby causing rotation of cutting element 4. The cutting element 4 is rotated about a longitudinal axis LA when the shaft 20 rotates. The cutting element 4 is rotated at about 1 to 160,000 rpm but may be rotated at any other suitable speed depending upon the particular application.

Opening 6 functions as a cutting window which may be a cutout opening in the distal portion of the catheter. As previously described, the cutting window should be long enough to collect tissue and circumferentially wide enough to allow the cutter to move out of the cutting window during cutting, but sized and shaped to not expel emboli into the vasculature.

As shown in FIG. 3, a flexible joint FJ is located proximal to the cutting window to provide a pivot point for camming of the distal portion relative to the proximal portion. The bending at flexible joint FJ is caused by the interaction of cams or ramps with the cutter and the tensile force provided through the drive shaft, as described previously. In exemplary embodiments, the distal housing can deflect off of the axis of the proximal portion of the catheter typically between 0 degrees and 30 degrees, usually between 5 degrees and 20 degrees, and most preferably between 5 degrees and 10 degrees. The angle of deflection relates directly to an urge force. A force urging the cutting window against the luminal wall of the vessel may be created by means of a pre-shaped curvature (not shown) in the region of the catheter proximal to the flexible joint in combination with the degree of deflection of the distal portion relative to the proximal portion. For example, the greater the angle of deflection, the larger the profile and the bigger the lumen that can be treated. The ranges set forth above allow treatment of vessels ranging from less than 2 mm to greater than 7 mm within the limits of mechanical design of the components. It should be appreciated however, that the angles of deflection will vary depending on the size of the body lumen being treated, the size of the catheter, and the like.

In some embodiments, the pre-shaped curvature of the distal portion of the catheter urges the cutter into position against the vessel luminal surface such that distal advancement of the entire catheter body can move the rotating cutter through the occlusive material. Because the cutter is moved a distance beyond the outer diameter of the distal portion of the catheter and outside of the cutting window, the user does not have to invaginate the tissue into the cutting window.

Pushing the entire catheter across a lesion removes all or a portion of the lesion from the body lumen. Severed tissue from the lesion is collected by directing it along the cup shaped surface of cutter 4 into a collection chamber in the distal tip 18. Once the catheter and cutter have moved through the lesion, the cutter can be advanced distally to a position in which the cutter is moved back through the cutting window and into the collection chamber. The tissue is collected as the severed pieces of tissue are directed into the collection chamber via the distal movement of cutter and catheter.

Figure 16A:
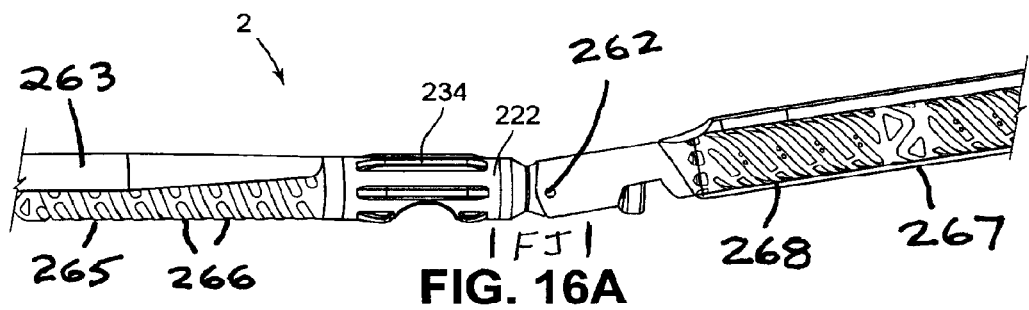
FIGS. 16A to 16C are side views of an alternate embodiment of the catheter of the present invention.
Figure 16B:
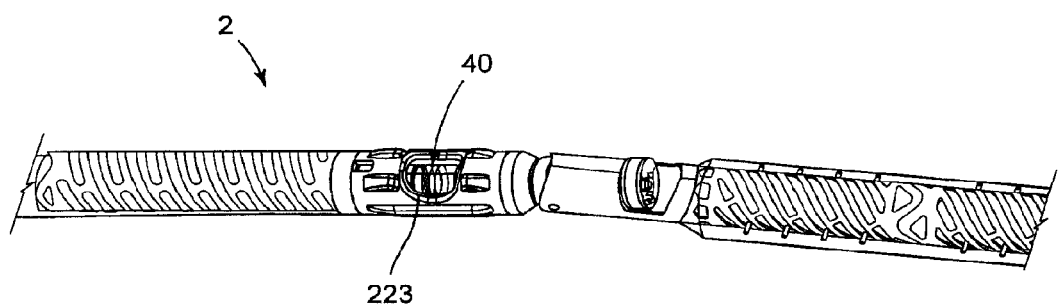
Figure 16C:
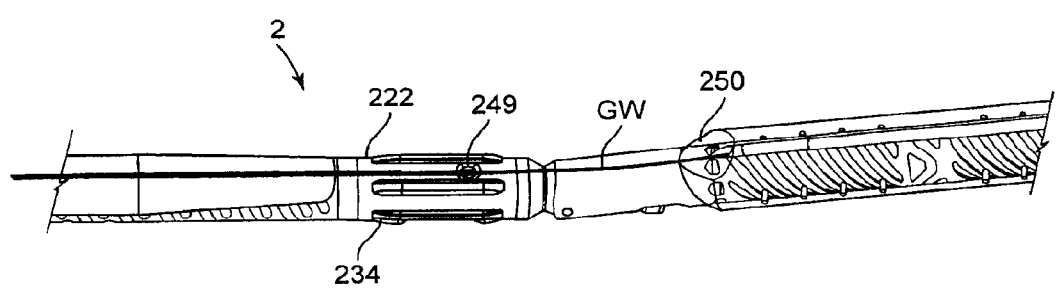

The catheter may be configured as an over the wire catheter or a rapid exchange or monorail catheter such as shown in FIG. 16C. For example, the tip of the catheter can include a lumen having a distal opening and a proximal opening that is sized to receive a guidewire, having a diameter of about 0.014 in., about 0.018 in., about 0.035 in. or any other suitable diameter.

Figure 5:
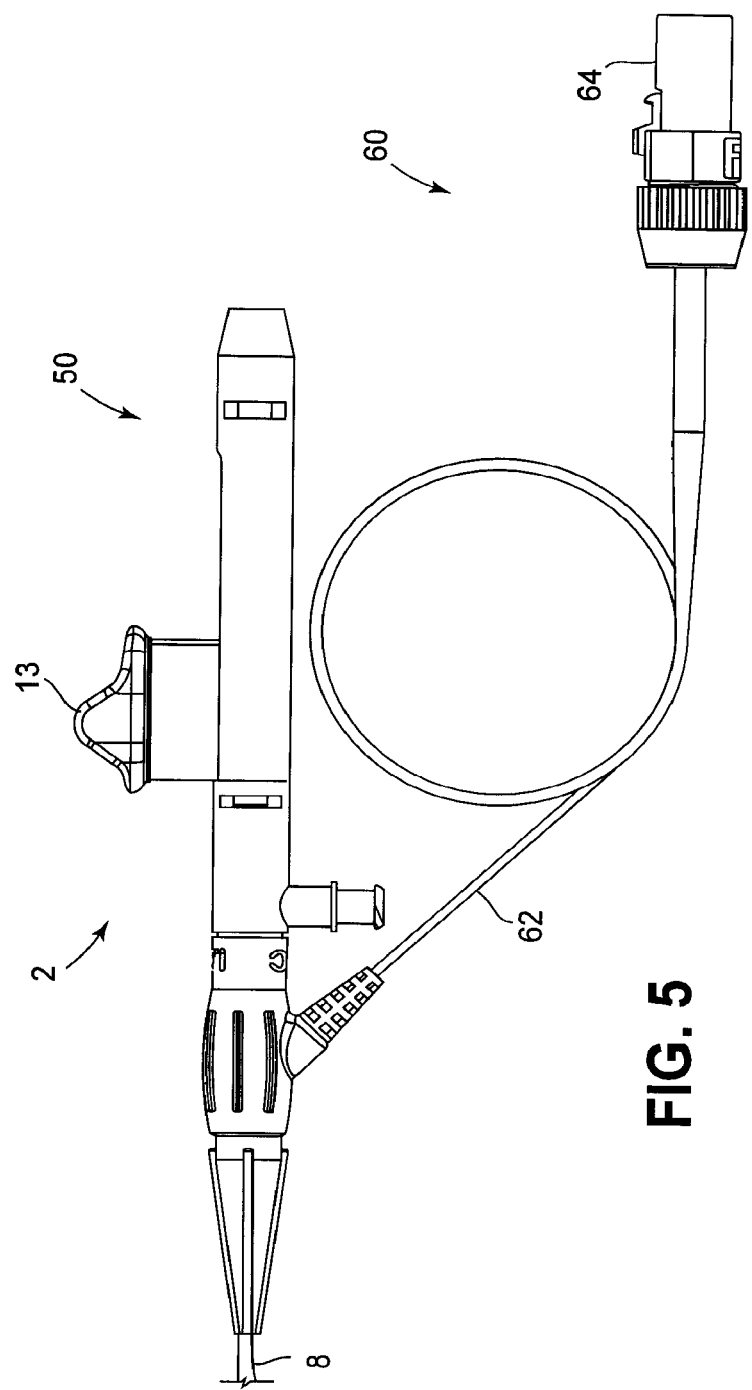
FIG. 5 is a side view of a portion of a catheter having ultrasonic imaging capabilities.
Figure 7:
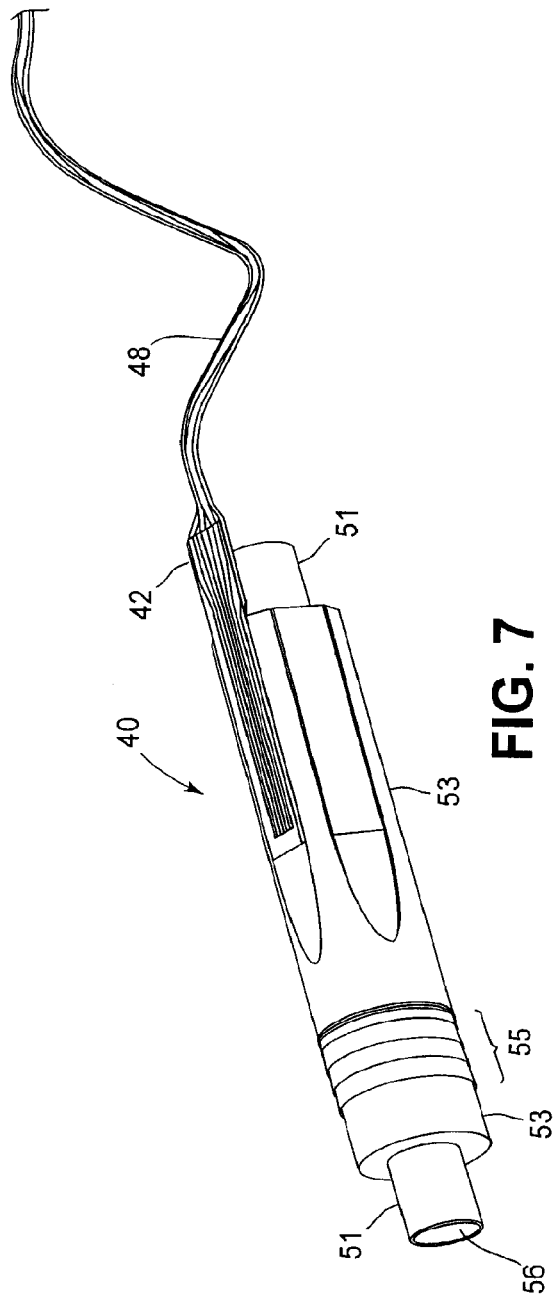
FIG. 7 is an isometric view of a transducer.

FIGS. 5, 6 and 7 illustrate catheter 2 having ultrasonic imaging capabilities located proximal to cutter 4. As shown in FIG. 5, catheter 2 is comprised of pigtail 60 and catheter body 8 attached to handle 50 having lever 13. Handle 50 is slideably received into cutter driver 5. Pigtail 60 is comprised of cable 62 and connector 64. Cable 62 is comprised of one or more electrically conductive wires 48 which travel within cable 62, connector 64 and lumen 47 of catheter body 8 so as to electrically connect connector to transducer 40, as shown in FIG. 7. Wires 48 may be comprised of insulated metallic wire, printed circuit board traces, or other insulated conductors. Connector 64 may electrically connect wires 48 to one or more non-catheter based components such as controls, signal processing components, signal conditioning components, Patient Interface Modules (PIM's), user interfaces, cables or other components.

As shown in FIG. 7, an exemplary transducer 40 is comprised of body 53, flex frame 42 and tube 51 having lumen 56 through which drive shaft 20 is slideably received. Tube 51 is comprised of stainless steel and extends beyond both distal and proximal ends of body 53. Flex frame 42 extends beyond proximal end of body 53 and electrically connects wires 48 to internal circuitry (not shown) of transducer 40. Body 53 houses electrical circuitry therein and has transducer elements 55 attached thereto. Transducer elements 55, in some examples piezo electric crystals, facilitate emission of image provoking sound pulses and reception of image signals. In some embodiments sound waves or pulses are in a frequency range of 1 MHz to 70 MHz, in other embodiments 10 to 30 MHz, or in still other embodiments 20 MHz. Typically transducer bodies 55 are rigid, similar to the rigidity of steel or engineering plastics where the materials of construction have Youngs Moduli in the range of 1,000,000 psi to 30,000,000 psi, and when they are mounted into catheters by conventional means the catheter may lose flexibility in the region of the transducer.

Figure 8A:
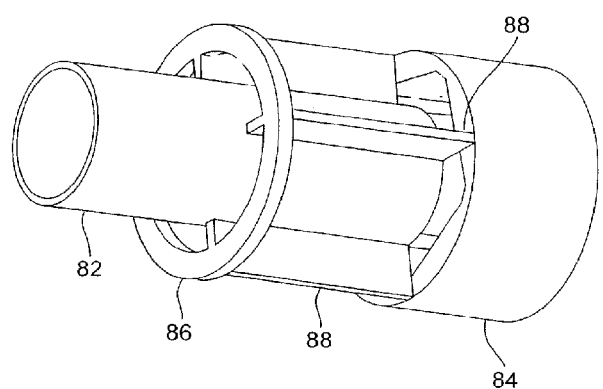
FIGS. 8A and 8B are isometric views of an embodiment of an adapter for use with a transducer.
Figure 8B:
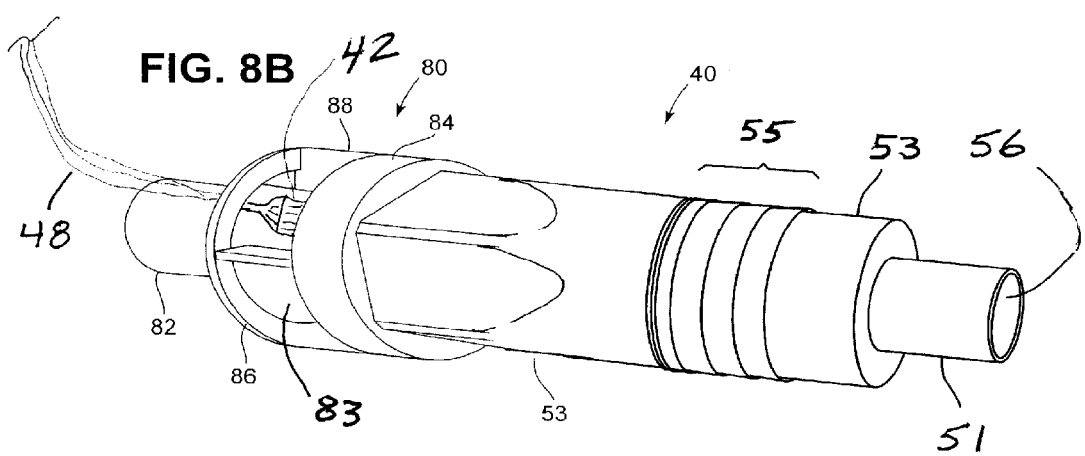

In some transducers, flex frame 42 is susceptible to damage, especially if the flex frame is bent, when transducer 40 is mounted into flexible catheters such as catheter 2. FIGS. 8A and 8B illustrate optional adapter 80 for use with transducer 40. Adapter 80 is comprised of tube 82, optional collar 84, optional ring 86, and struts 88; may be made of rigid materials such as steel, titanium, polyimide, polyester, engineering plastics, or other materials; and may be machined, molded, or made by other processes. In use tube 82 of adapter 80 is slid over and rigidly attached to tube 51 of transducer 40 using adhesives, welding, swaging, crimping, or other processes. Next potting material 83 is applied to adapter 80 to encase flex frame 42 and fill the gaps 87 between struts 88, rube 82, optional collar 84 and optional ring 86. Suitable potting materials 83 include flexible acrylics, silicones, urethanes and other materials having Young's Moduli typically in the range of 10,000 psi to 50,000 psi, in some cases about 30,000 psi. The adapter/transducer combination shown in FIG. 8B supports the flex frame so that it cannot flex as the catheter 2 flexes thereby preventing flex frame fracture. Further, tube 82 of adaptor 80 can extend beyond the potting material so as to provide a point of attachment for other catheter structures as will be described below.

FIGS. 9A and 9B illustrate alternative optional adapter 90 for use with transducer 40. Adapter 90 is comprised of inner tube 92, collar 94 and filler 96, each of which may be made of rigid materials such as steel, titanium, polyimide, polyester, engineering plastics, or other materials; and may be machined, molded, or made by other processes. In use inner tube 92 of adapter 90 is slid over and rigidly attached to tube 51 of transducer 40 using adhesives, welding, swaging, crimping, or other processes. Collar 94 is then slid over flex frame 42 of transducer 40 and attached to body 53 of transducer 40 using adhesives, welding, swaging, crimping, or other processes. Next filler 96 is applied to ends of inner tube 92 and collar 94 to encase flex frame 42 and transducer wires 48. Suitable fillers 96 include cyanoacrylate adhesive, stiff acrylic polymers, silicone polymers, urethane polymers and other materials having Young's Moduli typically in the range of 30,000 psi to 70,000 psi, in some cases about 50,000 psi. The adapter/transducer combination shown in FIG. 9B supports the flex frame so that it cannot flex as the catheter 2 flexes thereby preventing flex frame fracture. Further, inner tube 92 of adaptor 90 can extend beyond tube 51 of transducer 40 so as to provide a socket for attachment of other catheter structures as will be described below.

Referring again to FIG. 6, in one embodiment ultrasonic transducer 40 is mounted within catheter 2 generally parallel to catheter axis LA with the assistance of flexible filler 41, heat shrink 43, flex frame cover tube 45, optional transmissive material 44 and adhesive 46. Heat shrink 43 functions as a strain relief for wires 48 which are wrapped around heat shrink 43 so that motion of catheter body 8 proximal to heat shrink 43 is not transferred to flex frame 42. Heat shrink may be comprised of polyester or other materials. Flex frame cover tube 45 surrounds transducer 40 and flex frame 42. Tube 45 may be made of heat shrink comprised of polyester or other materials, and helps to prevent damage to flex frame 42 during catheter bending. Flexible adhesive 41 fills gap G between the transducer 40 and the flex frame cover tube 45 as well as any voids within catheter body 8 in the vicinity of transducer 40 and heat shrink 43 so that air or contamination in the voids is not introduced into the vasculature and to provide flexibility to the mounted transducer as described further below. Flexible filler 41 may be comprised of flexible acrylics, silicones, urethanes and other materials having Young's Moduli typically in the range of 1,000 psi to 30,000 psi, in some cases about 4,000 psi. Adhesive 46 adheres to one or more of transducer body 53 and catheter body 8. Suitable adhesive materials include cyanoacrylate adhesive, stiff acrylic polymers, silicone polymers, urethane polymers and other materials having Young's Moduli typically in the range of 30,000 psi to 70,000 psi, in some cases about 50,000 psi. Transmissive material 44 permits transmission of image provoking sound pulses and image signals therethrough, increases the diameter of transducer 40 to that of catheter body 8 so as to minimize ledges, angles, or other catch points along the catheter, and adheres to one or more of transducer elements 55 and catheter body 8. In the example of ultrasonic imaging, suitable transmissive materials for intravascular viewing match the acoustic impedance of blood and vascular tissue (approximated by the acoustical impedance of water, 1.5 MRayl) and have a low loss coefficient. Examples of suitable transmissive materials for any of the embodiments disclosed herein are listed in Table 1 below (courtesy of Onda Corporation, 592 Weddell Drive, Suite 7, Sunnyvale, Calif. 94089).

| Material | Acoustic Impedance (MRayl in MKS units) | Loss Coefficient (dB/cm at 5 MHz) |
| --- | --- | --- |
| Ethyl Vinyl Acetate | 1.6-1.7 | — |
| Polymethyl Pentene | 1.84 | ~4.2 |
| Acrylonitrile Butadiene Styrene | 2.36 | ~10.6 |
| Acrylic Epoxy | 3.1-3.3 | ~8 |

Optionally, transmissive material 44 may be coated with hydrophilic coating 49. Hydrophilic coating 49 assures good acoustical coupling of transmissive material 44 to the aqueous environment in which catheter 2 is used such as in blood, especially in cases where transmissive material may not be fully wetted with blood, for example, when the transmissive material may have good acoustical properties yet be hydrophobic. In some examples hydrophilic coating 49 may be comprised of polyvinyl pyrrolidone (PVP), polyvinyl alcohol (PVA), polyethylene glycol (PEG), polyethylene oxide (PEO), biologically active heparin, anticoagulant, or combinations thereof and may be ionically or covalently bonded to the underlying material. Such biocompatible hydrophilic coatings 49 may also improve the biocompatibility of the transmissive material surface by masking the surface from the body tissues.

Figure 10A:
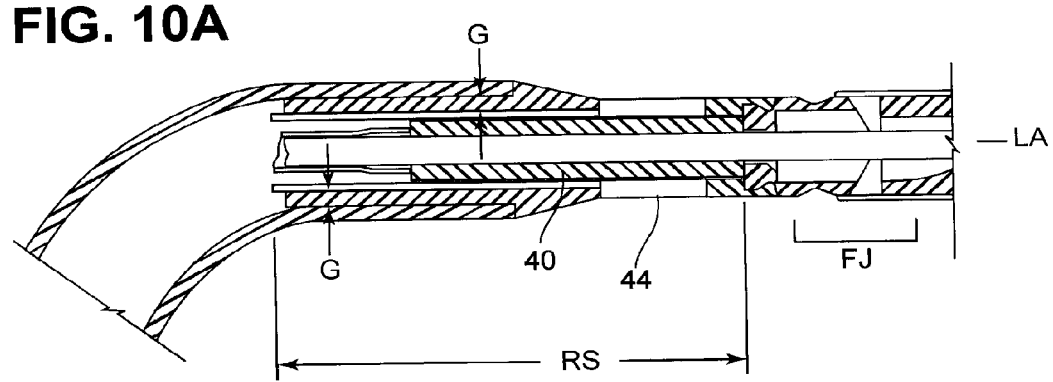
FIGS. 10A, 10B, 10C, 10D, 10E and 10F are cross-sectional side views of a portion of an atherectomy catheter.
Figure 10B:
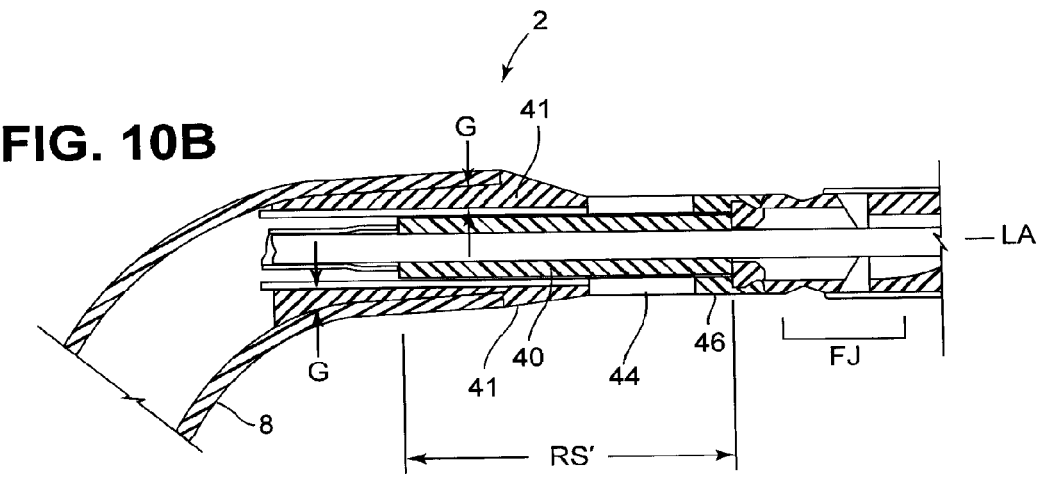

In the embodiment of FIG. 6 flexible filler 41 is more flexible than transducer body 53, adheres to catheter body 8 and the proximal end of transducer body 53, and fills gap G. In order to illustrate the advantage achieved by use of flexible filler 41 catheter 2 is shown in FIG. 10A with a conventional inflexible filler bridging gap G and in FIG. 10B with flexible filler 41. As shown schematically in FIGS. 10A and 10B, when catheter 2 is flexed in a direction transverse to axis LA flexible filler 41 will compress and elongate as needed to permit increased catheter bending flexibility in the vicinity of transducer 40 (FIG. 10B), whereas use of a conventional inflexible filler exhibits less flexibility in the vicinity of transducer 40 (FIG. 10A). The figures illustrate rigid section RS' in the vicinity of the transducer is shorter for the embodiment of FIG. 6 (as shown in FIG. 10B) than rigid section RS created by using conventional inflexible filler (as shown in FIG. 10A). Tensile and torsional strengths of the catheter section are preserved because of the adhesive connections between the transducer body and catheter body 8.

In an alternative embodiment, one of the ends of transducer 40 may be welded to a proximal end of flexible joint FJ. For example, the distal end of transducer tube 51 may be welded to a proximal end of flexible joint FJ and the proximal end of transducer tube 51 may be flexibly bonded to catheter body 8 as shown in FIG. 10B. When catheter 2 is flexed, filler 41 will compress and elongate as needed to permit increased catheter flexibility at the proximal end of transducer 40 and flexible joint FJ at the distal end of transducer 40 will also permit catheter bending in the vicinity of the joint. Tensile and torsional strengths of the catheter section will be preserved because of the adhesive connection between the transducer body and catheter body 8 and the weld between the distal end of transducer 40 and the joint.

Figure 10C:
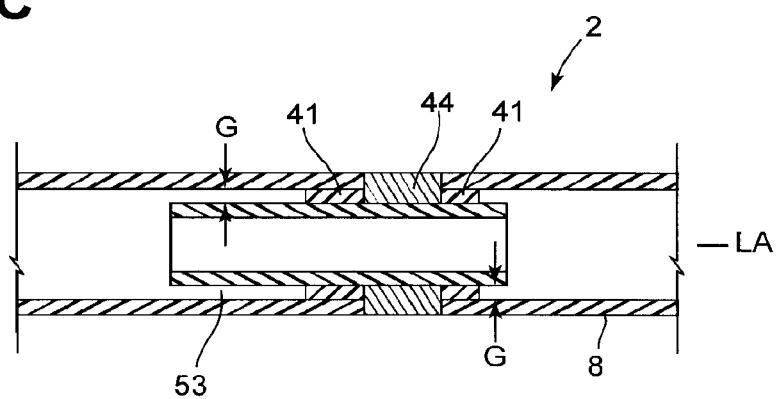
Figure 10D:
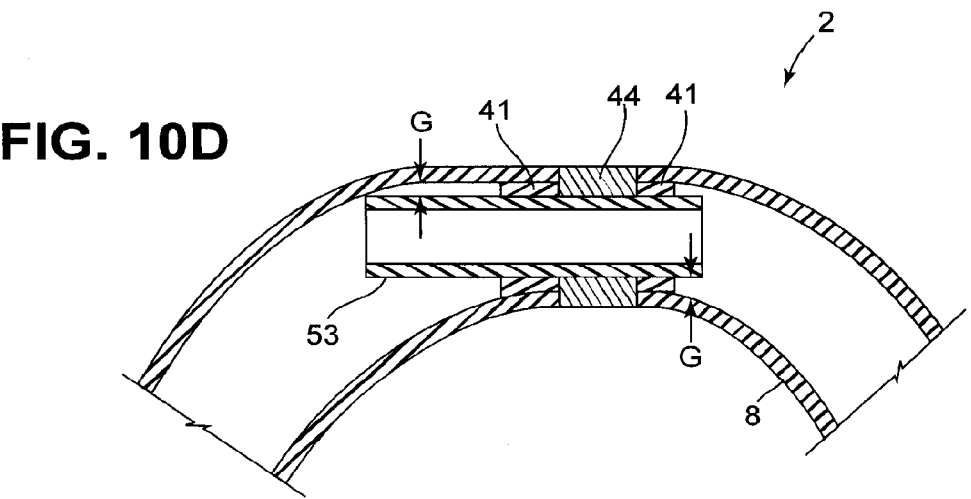
Figure 10E:
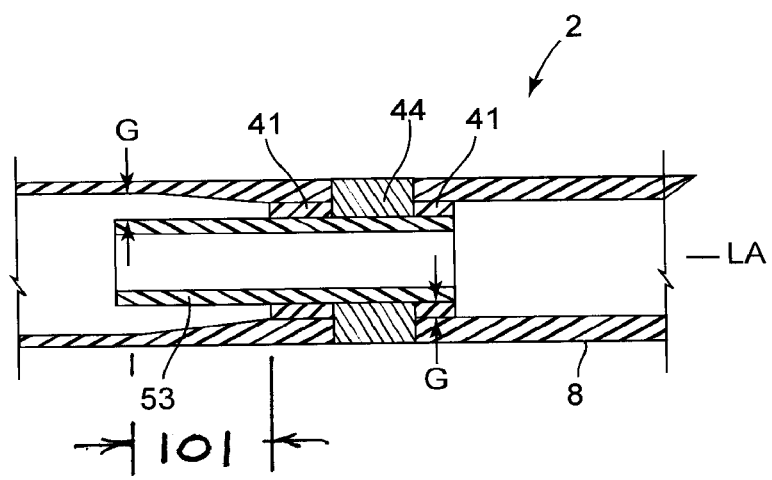
Figure 10F:
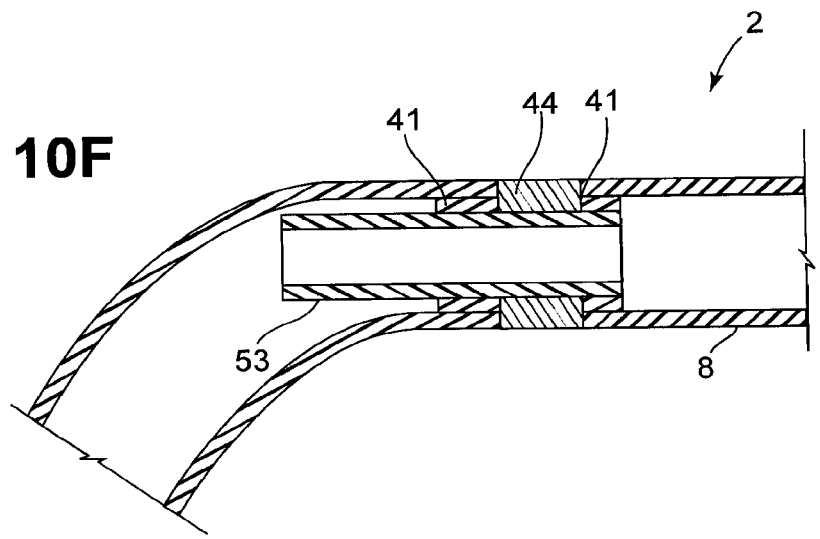

FIGS. 10C, 10D, 10E and 10F illustrate further embodiments of catheter 2. FIGS. 10C and 10D show an embodiment of catheter 2 where filler 41 bonds both ends of transducer body 53 to catheter body 8 and does not extend over the entire length of the annular gap G between transducer body 53 and catheter body 8. When catheter 2 bends less filler 41 in gap G needs to be stretched or compressed as compared to the embodiment shown in FIGS. 10A and 10B. FIGS. 10E and 10F show an embodiment of catheter 2 where the wall thickness of catheter body 8 is reduced along a region 101 in the vicinity of transducer body 53 so as to permit increased catheter flexibility in the vicinity of transducer 40 and to establish a longer gap G.

FIG. 11 illustrates catheter 2 having ultrasonic imaging capability, transducer 40 and drive shaft strain relief 110 attached to one or more of tube 51 of transducer 40, inner tube 82 of adapter 80 or inner tube 92 of adaptor 90 using adhesives, welding, swaging, crimping, or other processes. Strain relief 110 is compatible with the embodiments of FIGS. 6, 7, 8A, 8B, 9A, 9B, 10B, 10C, 10D, 10E, 10F, 15 and could be optionally used with any of the other embodiments disclosed herein. Strain relief 110 may be comprised of thin walled tubing made of stainless steel, titanium, Nitinol or other materials and may have one or more slits or apertures along its length so as to vary its flexibility. Strain relief lengths in non-limiting examples range from 25% of transducer length to 200% of transducer length and also generally from 5 mm to 50 mm in length. Strain relief inside diameter is sized to provide a longitudinally and rotationally sliding fit over drive shaft 20 and can be lined with a slippery material such as PTFE, FEP, silicone lubricant, or other materials or lubricants, said lining configured as a coating, a tube, a grease, or other configurations.

Strain relief 110 functions to prevent an abrupt bend of drive shaft 20 at the end of tube 51 (at E in FIG. 11) thereby improving fatigue life of rotating drive shaft 20. Strain relief 110 also prevents concentrated friction of drive shaft 20 against luminal wall of catheter lumen 21 thereby preventing localized heating of drive shaft and catheter body 8. Strain reliefs comprised of metal can also dissipate heat by conduction or by radiation away from the end of tube 51. Strain relief 110 also prevents end of tube 51 from abrading drive shaft 20 when catheter 2 is bent transverse to longitudinal axis LA.

Figure 12:
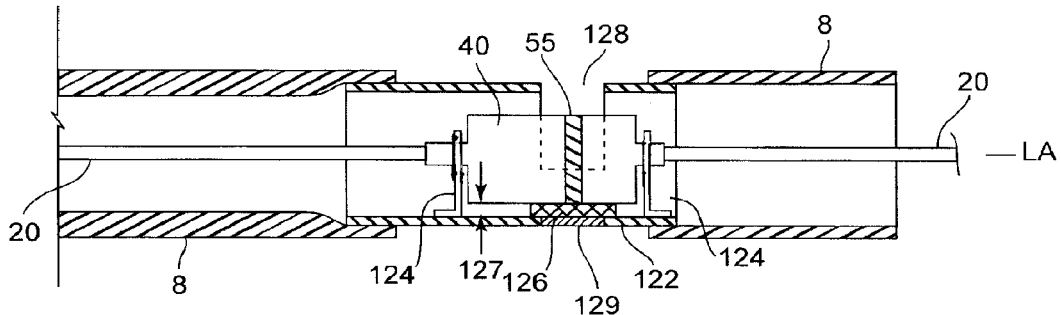
FIG. 12 is a partial cross sectional side view of a transducer mounted into a catheter.
Figure 13A:
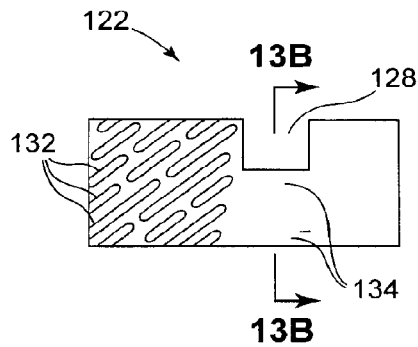
FIGS. 13A and 13D are side views of portions of the catheter illustrated in FIG. 12.
Figure 13B:
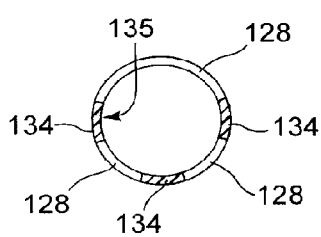
FIG. 13B is a partial cross sectional end view of a portion of the catheter illustrated in FIG. 12 taken along section 13B of FIG. 13A.
Figure 13C:
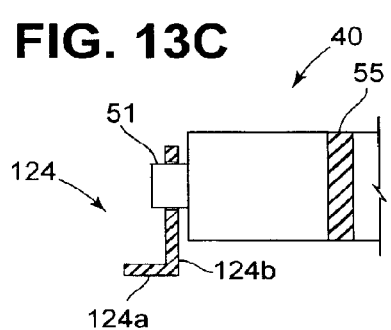
FIG. 13C is a partial cross sectional side view of a portion of the catheter illustrated in FIG. 12.
Figure 13D:
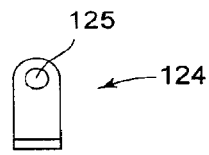

FIGS. 12, 13A, 13B, 13C, and 13D illustrate an alternate embodiment of catheter 2 in which transducer 40 is held within catheter body 8 in a manner that allows transducer 40 to essentially float within catheter body 8. As shown in FIG. 12 which is a partial cross-sectional side view, catheter 2 is comprised of catheter body 8, drive shaft 20, transducer housing 122, brackets 124, transducer 40, and optionally, hydrophilic material 126 and windowpane 129. Catheter body 8, drive shaft 20 and transducer 40 have been described previously. Housing 122 is attached at both proximal and distal ends to catheter body 8 using adhesives, welding, swaging, crimping, or other processes and may be comprised of stainless steel, nitinol, polyimide, transmissive materials 44, or other materials. Housing 122 has one or more windows 128 therein as well as one or more elongate openings 132 cut through the wall of housing 122 and internal coating 135. Struts 134, defined by the elongate openings 132, connect proximal and distal portions of housing 122 in the vicinity of windows 128. Windows 128 are axially aligned with transducer crystals 55 and allow ultrasonic sound pulses to travel between transducer crystals 55 and vessel wall, while elongate openings 132 confer flexibility to housing 122. Struts 134 may be integral portions of housing 122 or may be comprised of other materials attached to housing by means of welding, bonding, or other processes. Strut 134 thickness and materials of construction may be adjusted to confer either more or less stiffness to housing in the vicinity of windows 128 transverse to axis LA. Internal coating 135 absorbs or scatters ultrasonic sound pulses and may be comprised of silicone rubber, urethane, or other materials.

Figure 14:
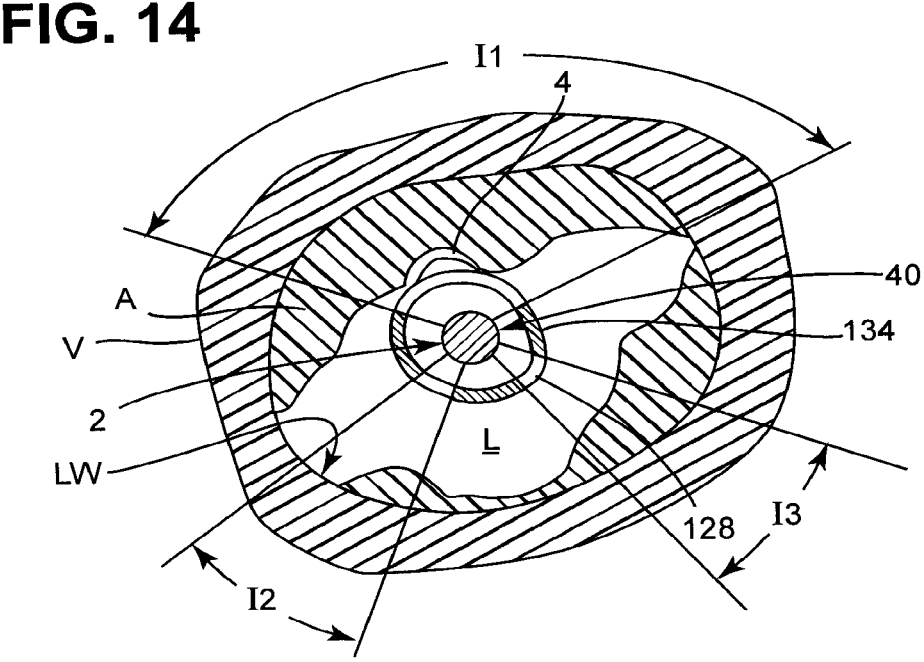
FIG. 14 is a partial cross sectional view of an atherectomy catheter having an imaging transducer catheter in use.

In some embodiments window locations are positioned to allow imaging of pre-determined portions of a vessel wall. FIG. 14 shows an embodiment wherein catheter 2 is positioned inside lumen L of vessel V having luminal wall LW with atheroma A attached thereto. In the embodiment disclosed in FIGS. 12, 13A, 13B, 13C and 13D, ultrasonic sound pulses generated by transducer 40 will be absorbed or scattered by internal coating 135 so that reflections from the internal surface of the housing back to the transducer will be minimized, thereby improving image signal to noise ratio. Ultrasonic sound pulses generated by transducer 40 will pass through windows 128 until they contact vessel V and are reflected back to transducer 40. In one embodiment, windows 128 may be sized and positioned such that a wide circumferential image I1 is produced in the vicinity of cutter 4 and smaller circumferential images I2, I3 are produced on the opposite side of the catheter from which the cutter is located. One advantage of this window configuration is that the circumferential location of cutter 4 relative to image I1 is immediately apparent as such location is always centered on the largest window. Another advantage of this window configuration is that atheroma adjacent to that portion previously cut by cutter 4 (if any) is visible and further atheroma removal, if needed, can be planned. Other window numbers and placements are possible for any of the embodiments disclosed herein in order to produce images having desired features.

Returning to FIGS. 13A, 13B, 13C and 13D, brackets 124 are comprised of foot 124a and leg 124b having hole 125 therein, as best seen in FIGS. 13C and 13D, and may be comprised of stainless steel, nitinol, polyimide or other materials. Hole 125 is sized to provide a longitudinally and rotationally sliding fit over tube 51 of transducer 40. In the embodiment of FIG. 12 two brackets are used, one located at each end of transducer 40 and attached to housing 122 using adhesives, welding, swaging, crimping, or other processes. As shown in FIG. 12, brackets 124 generally center tube 51 of transducer within catheter body 8 and establish gap 127 between transducer 40 and inner surface of housing 122. Thus, brackets 124 hold housing 122 in a manner allowing it to essentially float within catheter body 8.

In some embodiments windows 128 are provided with windowpanes 129 comprised of transmissive material 44. Hydrophilic material 126 fills the gap 127 between transducer crystals 55 and transmissive material 44, and may be attached to either crystals 55 or transmissive material 44 or both. In other embodiments hydrophilic material 126 fills all free volume within housing 122 that is not occupied by solid components such as transducer 40, adapter 80, 90, bracket 124, or other solids. Hydrophilic material 126 ultrasonically couples crystals 55 to transmissive material 44 thereby reducing or eliminating sound reflections from the surfaces of either or both and may be comprised of polyvinyl pyrrolidone (PVP), polyvinyl alcohol (PVA), polyethylene glycol (PEG), polyethylene oxide (PEO), or combinations thereof. In some embodiments hydrophilic material is hydrated with aqueous media such as saline, heparinized saline, or other media prior to introduction of catheter 2 into a patient's body.

Figure 15:
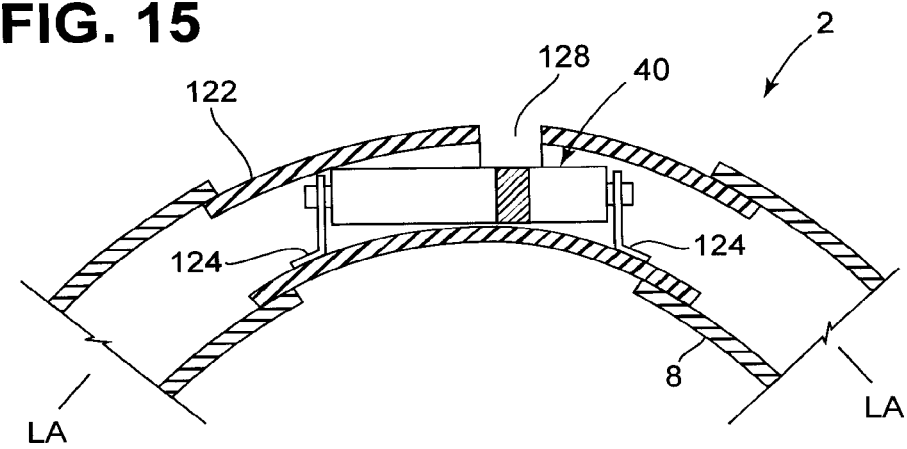
FIG. 15 is a partial cross-sectional side view of a portion of an atherectomy catheter.

As shown in FIG. 15, the manner in which transducer 40 is carried in transducer housing 122 allows transducer 40 to float radially within catheter body 8 when catheter 2 is bent transverse to its longitudinal axis. Tensile and torsional strengths of the catheter section will be preserved because of the connections between the housing 122 and catheter body 8. When bent, gap 127 of catheter 2, as shown in FIG. 12, is generally reduced on both the convex and concave side of the bend. Resistance to gap reduction or gap enlargement is low because gap 127 is not filled with any solid substance. Also rigid section RS in the vicinity of the transducer (described earlier in connection with FIGS. 10A and 10B) is non-existent over a range of catheter bends due to the suspension of transducer 40 on brackets 124. Optionally, strain relief 110 as described earlier can be added to one or both ends of transducer 40.

Figure 16D:
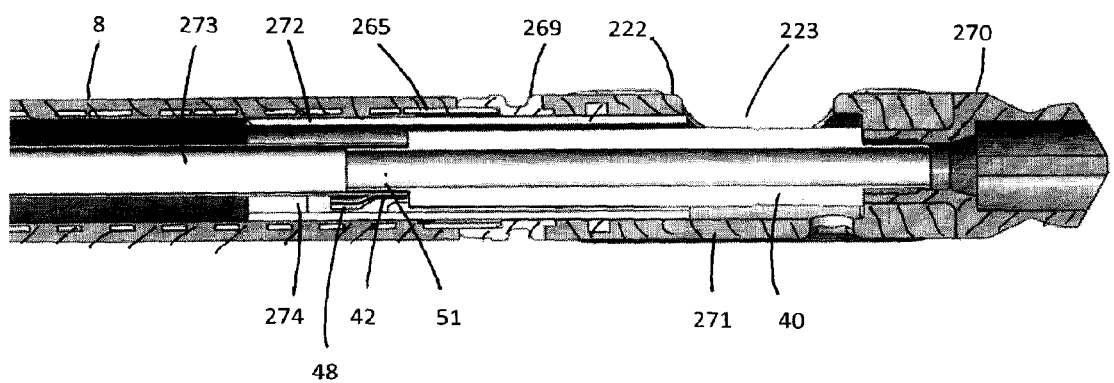
FIG. 16D is a cross-sectional side view of a portion of the catheter shown in FIGS. 16A to 16C.

FIGS. 16A to 16D illustrate an alternate embodiment of catheter 2 in which transducer 40 is housed within a transducer housing 222 (shown in FIGS. 17A to 17D) in catheter body 8. FIGS. 16A to 16C are side views from different orientations of a portion of catheter 2 that includes housing 222, connected between a proximal segment of catheter body 8 and a distal tip assembly 267. FIG. 16D is a side sectional view through the central axis of catheter 2. Housing 222 houses and protects transducer 40, which may be fragile and prone to breaking as the catheter is advanced in the vessel or lumen, by carrying or translating the mechanical stresses and forces surrounding transducer 40. Thus, housing 222, by carrying or translating the stresses and forces, is intended to isolate transducer 40 from these stresses and forces in and around the catheter, and transmit such stresses and forces through the housing from the proximal end of the housing to the distal end of the housing thus reducing the stresses and forces to which the transducer is subjected. Housing 222 is attached at a proximal end to catheter body 8. For purposes of illustration an outer layer 263 of catheter body 8 is shown partially transparent in order to show the structure of catheter body 8 in FIGS. 16 A to 16 C. In order to enhance both the flexibility and strength of catheter body 8 proximal to housing 222, catheter body 8 is formed of a tube 265 which is provided with elongate openings 266 to enhance the flexibility of the tube. Tube 265 may be fog need from a stainless steel hypotube which has been laser cut to form the openings. Alternatively, tube 265 might be formed from material such as titanium, polyimide, polyester, engineering plastics or other materials having similar properties. A distal tip assembly 267 of catheter body 8 distal of the housing 222 may comprise a tube 268 having the properties of tube 265.

Housing 222 is shown in side, top, axial cross-section and transverse cross-section in FIGS. 17A, 17B, 17C and 17D, respectively. Housing 222 may be of multipart construction which includes a proximal end portion 269, a distal end portion 270 and a body portion 271. The proximal and distal end portions 269 and 270 may be formed from first and second materials, respectively, which are different from a third material forming body portion 271. For example, the first and second materials may comprise a metal such as titanium or stainless steel and the body portion 271 may comprise a polymer. In one embodiment the distal end portion 270 comprises titanium, the proximal end portion 269 comprises stainless steel and the body portion 271 comprises acrylonitrile butadiene styrene (ABS). The first and second materials are selected to provide transducer housing 222 with sufficient strength at its distal and proximal ends and to enable the housing 222 to be securely connected to the proximal portion of the catheter body 8 and the distal tip assembly 267. The third material forming the body portion 271 of housing 222 is selected to provide the housing with sufficient flexibility. The third material is also selected from materials that minimize any interference with or distortion of the transducer signals or images sent or received through the third material or through slot 223 in the third material.

In one embodiment the transducer housing 222 is formed by a process that combines or joins the body portion 271, distal end portion 270 and proximal end portion 269 into a single integrated part. For example, the transducer housing may be formed utilizing an injection molding process in which the body portion 271 is overmolded onto the proximal and distal end portions 269 and 270. This results in the formation of a single integrated housing 222 that has desired properties of strength, flexibility and connectability.

FIG. 16D is a cross-sectional view of housing 222 connected to a portion of catheter body 8. As shown in FIG. 16D, a portion of transducer 40 proximal of slot 223 is contained within a tubular member 272. Tubular member 272 is formed from a rigid material which functions to protect transducer 40, flexframe 42 and wires 48 during use of the catheter. In one embodiment tubular member 272 comprises a stainless steel hypotube. Tubular member 272 has a lumen with an inner diameter sized to accommodate the transducer 40. The transducer 40 is secured within the tubular member 272 using a suitable potting material. The transducer 40 and tubular member 272 are inserted during assembly within the housing 222 so that transducer elements of transducer 40 are axially aligned with slot 223. Tubular member 272 and transducer 40 may be entirely contained within an interior space of the housing 22 or, as shown in FIG. 16D, may be positioned such that at least distal portions of both tubular member 272 and transducer 40 are received with housing 222. The tubular member 272 is then welded or otherwise attached to the proximal end portion 269 to fix the tubular member 272 and transducer 40 within housing 222. A distal portion of tube 265 is sized to be received within a proximal portion of proximal end portion 269 in an overlapping arrangement. The proximal end portion 269 is then welded or otherwise attached to tube 265 in this overlapping region. As shown in FIG. 16D, tube 265 may be integrated into catheter body 8 in a manner that results in the material forming catheter body being received within openings 266 in tube 265. For example, tube 265 may be laminated within catheter body 8 so that the material forming the catheter body infiltrates into the elongate holes in tube 265.

A transition tube 273 having an interior diameter slightly larger than an end 51 of transducer 40 may overlap with and extend from end 51 of transducer 40. The transition tube 273 may be potted within the tubular member 272 with a potting material 274 to attach it within the housing 222. The transition tube 273 functions to protect and isolate flexframe 42 and wires 48 from the drive shaft 20 which is omitted from FIG. 16D in order to more clearly show the other features described herein. A continuous lumen is formed through catheter body 8, transducer 40 and transition tube 273 to accommodate the drive shaft 20 which extends through the lumen distally past the housing 222 for attachment to the cutter element 4 positioned within the distal tip assembly 267.

Figure 17A:
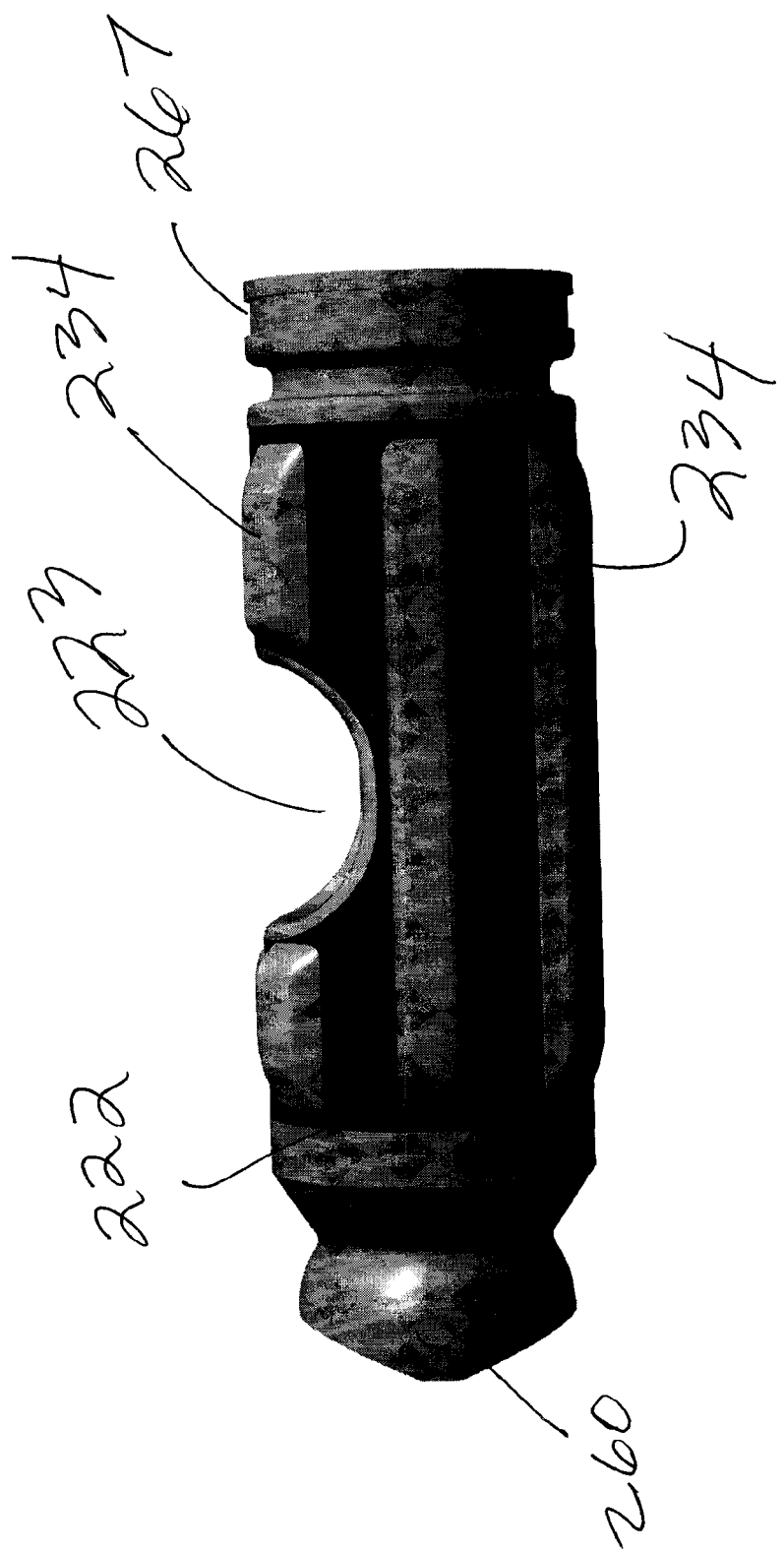
Figure 17C:
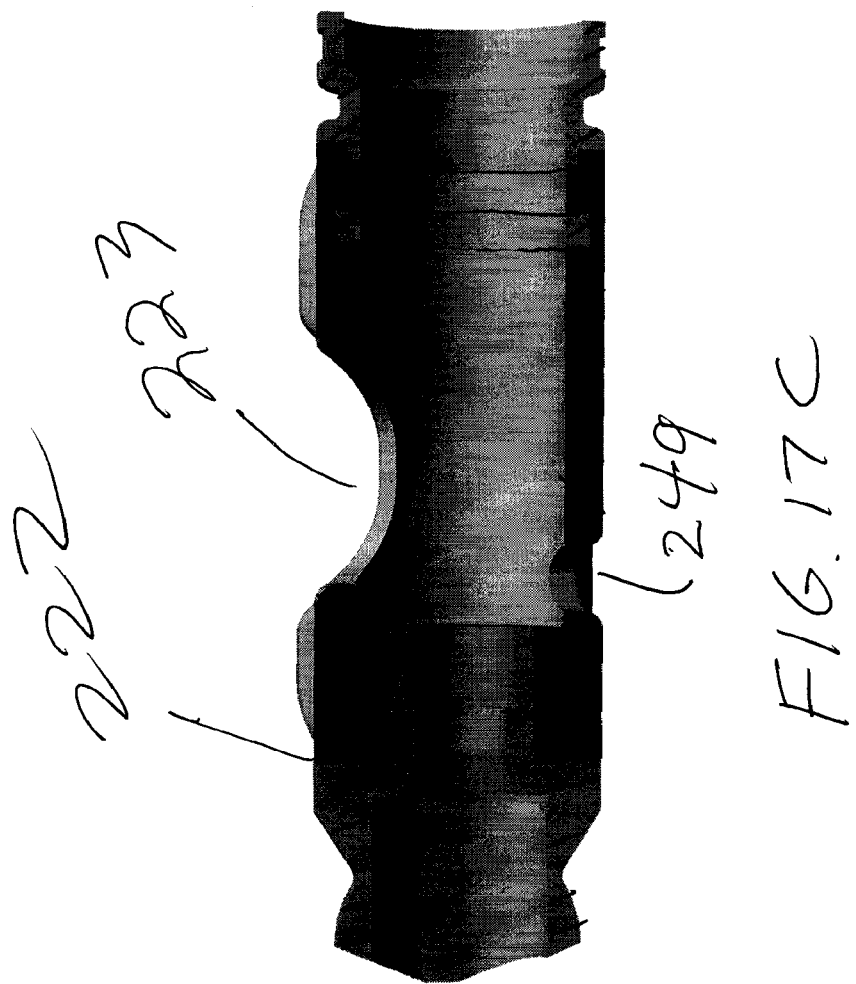

In the embodiment shown in FIGS. 16A, 16B and 16C the flexible joint FJ is formed by a hinged connection formed by joining the distal end portion 270 of transducer housing 222 to the distal tip assembly 267. As shown in FIG. 17A the distal end portion 270 of housing 222 has a pair of pin holes 260 positioned on opposite sides of the distal end portion 270. During assembly, pin holes 260 are aligned with opposing pin holes 262 (shown in FIGS. 16A to 16C) in distal tip assembly 267. A pin is then inserted through the aligned pin holes on both sides of the catheter and welded to the distal tip assembly 276. The pins are thus fixedly connected to distal tip assembly 267 in pin holes 262 and movably received in pin holes 260 of housing 222. The result is the formation of a hinged joint connecting the distal end portion 270 of transducer housing 222 to the distal tip assembly 267 allowing the distal tip assembly 267 to pivot with respect to the housing 222 and proximal portion of catheter 2 at the hinged joint.

The outer wall of the housing may have a thickness that minimizes acoustic attenuation by allowing better penetration through the housing of the acoustic ultrasound signal produced by the transducer thus improving the quality of imaging and may be, for example, 0.008 to 0.020 inches thick. In order to better preserve the structural integrity of housing 222, ribs 234 may be provided. The ribs 234 may be pieces or portions which are molded on the outer surface of the housing or attached to the outer wall of the housing by means of welding, bonding, adhesives, etc. Alternatively, the housing 222 and ribs 234 may be integrally formed such that the outer surface of housing 222 is contoured with outward projections forming the ribs. Ribs 234 strengthen or reinforce the wall of housing 222 and increase the moment of inertia of the outer wall of the housing. Thus, the ribs 234 increase the structural integrity of the housing and protect the housing from the forces created by the use of catheter 2 in a vessel. The ribs also reduce the stress on the housing and reduce the possibility of over-bending, breaking, crimping, etc. The materials of construction and dimensions (i.e., length, width and height) of ribs 234 may be adjusted to confer either more or less stiffness to the housing in the vicinity of slot 223. The materials of construction and dimensions may also be modified to adjust the outer diameter or the circumference of housing 222. Additionally, the amount and spacing of ribs 234 on the outer wall of housing 222 is not limited, thus the number of ribs, as well as the spatial separation of the ribs, may be increased or decreased as desired and can, for example, be in the range of 5 to 8 ribs located at equal or differing spatial dimensions around the circumference of housing 222. The ribs may be elongate and be positioned such that they are substantially parallel with the longitudinal axis of the housing and catheter. The diameter of housing 222 of the non-ribbed surface may be 0.083 inches wide to maintain a 7 French guide catheter or sheath compatibility as an example.

Figure 17D:
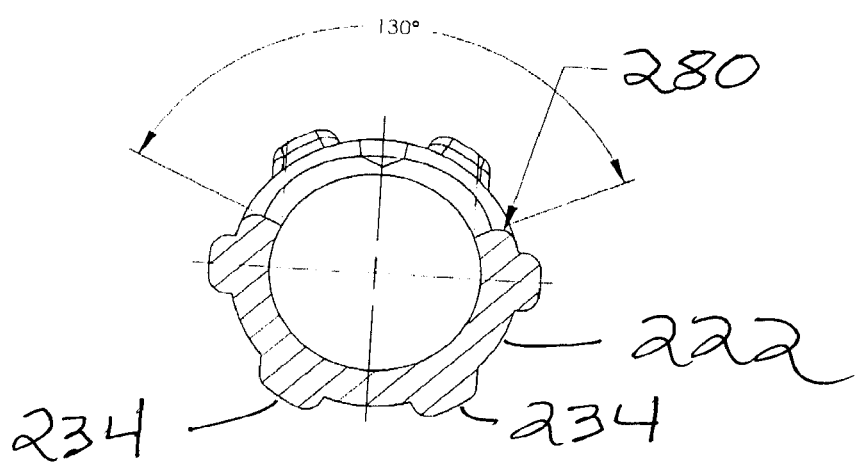
Figure 18A:
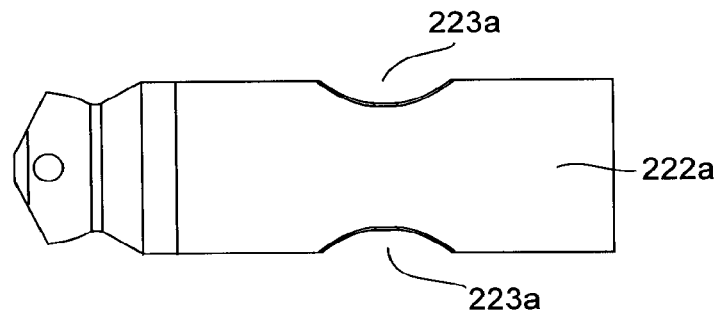
FIGS. 18A to 18D are side, top and cross-sectional views of an alternate embodiment of a transducer housing of the catheter of FIGS. 16A to 16C.
Figure 18B:
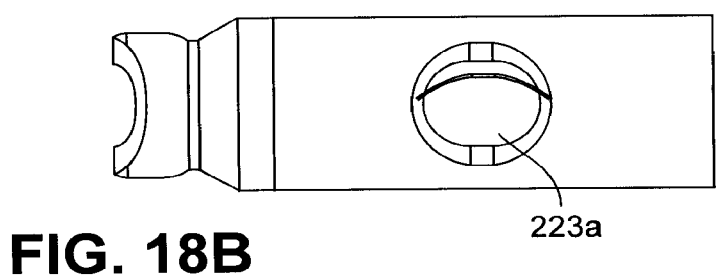
Figure 18C:
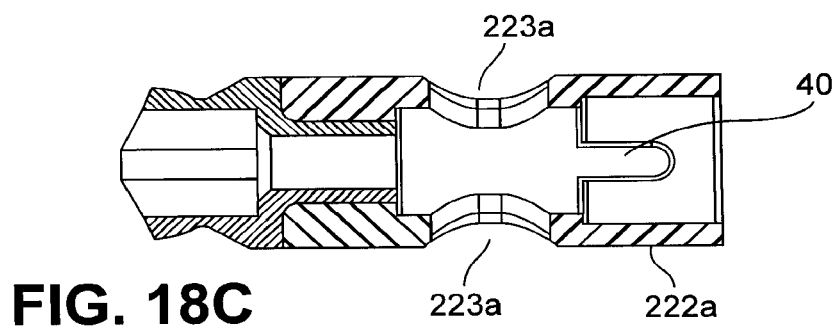
Figure 18D:
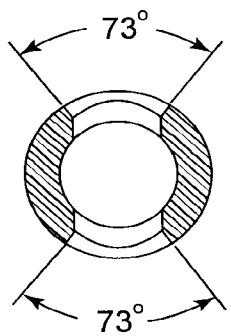
Figure 19A:
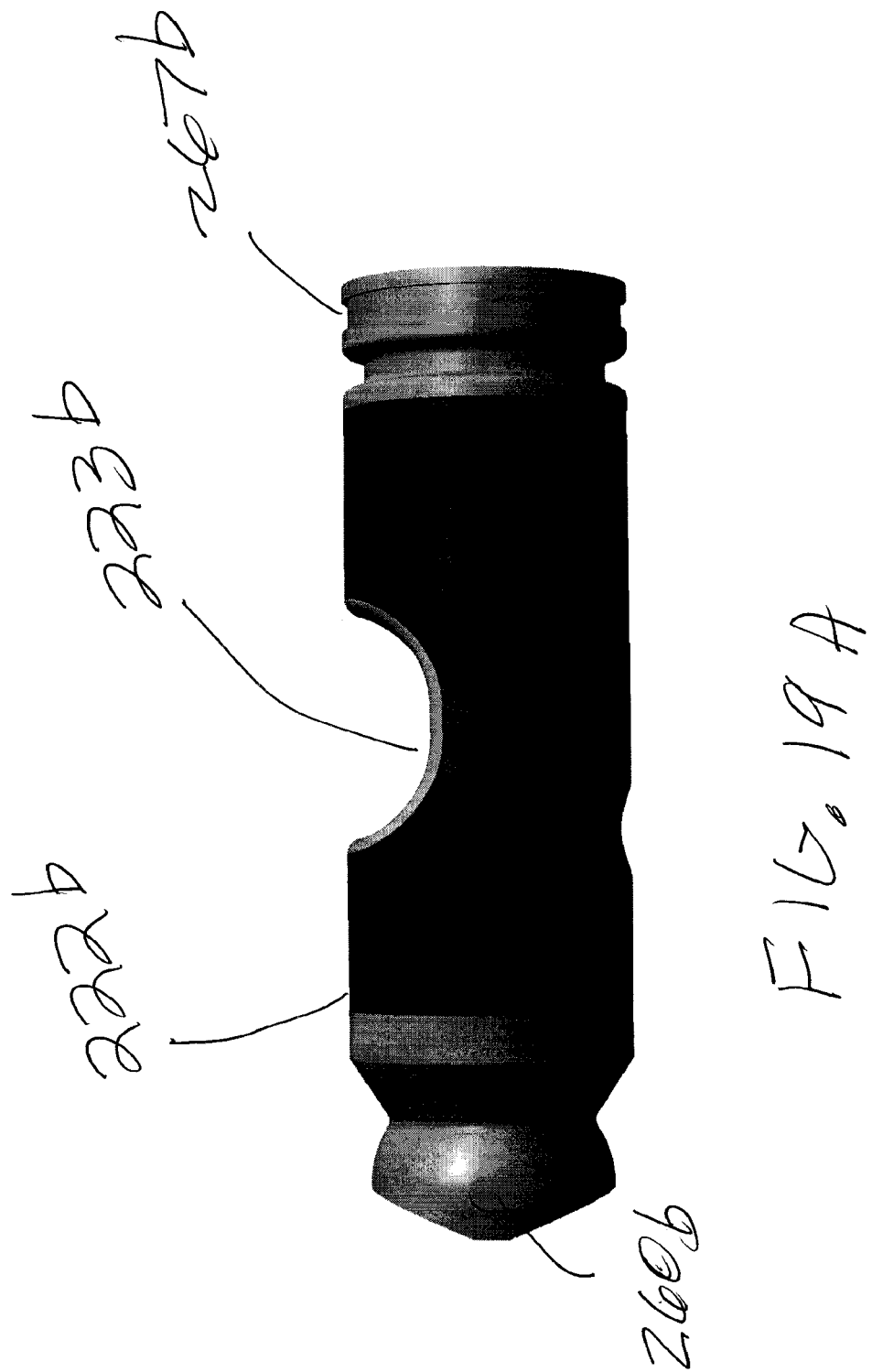
Figure 19B:
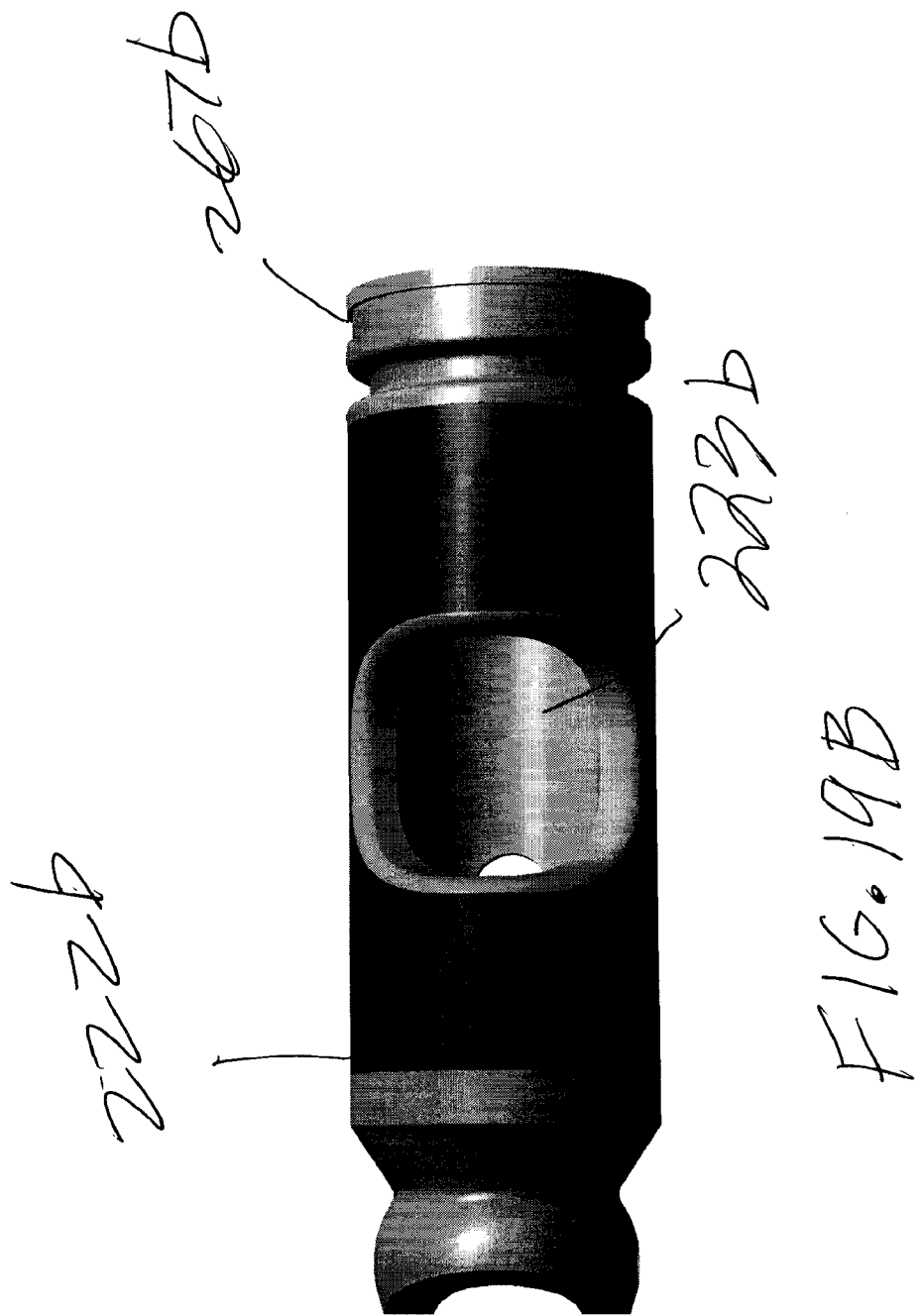
Figure 19D:
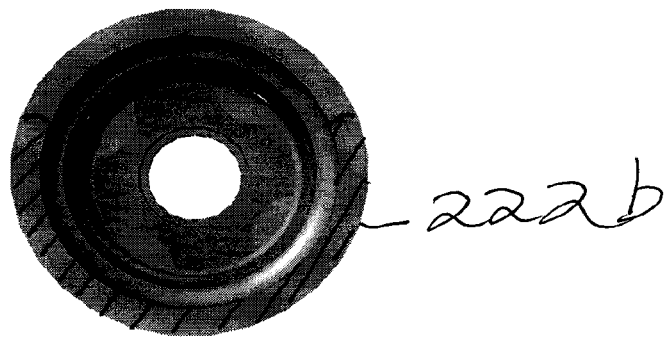

Outer wall of housing 222 has slot 223 which is axially aligned with the transducer crystals of transducer 40 allowing acoustic ultrasonic sound pulses to travel between transducer crystals and the vessel wall in such a way as to minimize attenuation or interference. The transducer 40 will produce a 360° image of the vessel through the outer wall of housing 222 and slot 223. However, the radial angled portion of the 360° imaged vessel obtained through slot 223 may be of a higher quality than the remainder of the radial angled portion of the 360° imaged vessel obtained through the outer wall of housing 222, thus a larger dimensioned slot may be preferred. Slot 223 may be sized to provide a radial scanning angle of the imaged vessel in the range of 60° to 180° of the circumference of the housing and may be more specifically in the range of 120° to 150° and further may be 130° as can be seen in FIG. 17D. To minimize any effect of distortion and to minimize the amount or size of any artifacts in the image, the edges 280 of the opening of slot 223 may be shaped or angled to coincide with the radius of the catheter, as best seen in FIG. 17D.

Slot 223 may be positioned directly proximal of the cutting window so the physician is able to view with greater clarity and accuracy what has just been cut or removed at a treatment site in a vessel or lumen as the catheter is advanced distally in the lumen with the cutting element in the working position. Alternatively, slot 223 may be positioned at other locations along the catheter body. Additionally, the catheter could be advanced distally in the lumen with the cutting element in the stored position until slot 223 is adjacently aligned with the treatment site so that the physician is able to view with greater clarity and accuracy what is about to be cut or removed from the treatment site.

Slot 223 provides an opening into the lumen of the housing which allows blood or other fluid to be in direct contact with the outer surface of the transducer thereby improving the quality of the image produced by improving the acoustical coupling of the sound waves from the transducer, through the fluid, and to the lumen wall. The urge created by the bend in catheter 2 may result in housing 222 being pushed against a vessel wall, potentially distorting or interfering with the image quality produced by the transducer, especially at the area of housing where slot 223 is located. Ribs 234 also function to space the housing away from any direct contact with a vessel wall created by such urge of the catheter. The spacing allows fluid in the vessel to more freely flow between the housing and the vessel wall, and between the transducer and vessel wall when slot 223 is directly opposed to the vessel wall. This spacing improves image quality and image resolution.

Slot 223 may have a longitudinal width of 0.070 inches and a transverse width of 0.055 inches. It should be understood that the slot 223 of housing 222 could have any desired dimension depending upon the application and that housing 222 may have multiple slots located in the outer wall of the housing. For example, housing 222 could have 2 (as shown in the embodiment of FIGS. 18A to 18D), 3 or 4 slots as desired.

Catheter 2 may be provided with a saline source connected to a saline pump or drip located at the proximal end of the catheter (not shown) to maintain a positive pressure of saline flowing through the lumen of the catheter. The positive pressure created by the saline pump allows the saline to flow/move through the lumen and prevents air from becoming trapped or enclosed in the lumen of the catheter. The quality of the image produced by the acoustic ultrasound pulses of the transducer are improved if fluid is maintained within housing 222. Therefore catheter 2 may be provided with a gap or spatial dimension between the inner diameter of the outer wall of the housing and the outer diameter of the transducer, allowing the saline to flow into the housing. The spatial gap between the inner diameter of the outer wall of the housing and the outer diameter of the transducer may additionally allow blood from the vessel to enter into the housing through slot 223 both preventing air pockets from being trapped in the housing 222 and maintaining fluid over the transducer. The gap or spatial dimension between the housing 222 and the transducer 40 may be in the range of 0.003 to 0.009 inches and further may be 0.007 inches but could be wider or narrower, as desired. Housing 222 may also be provided with weep hole 249 through which fluid may exit the housing to improve fluid flow through the lumen of the catheter generally and in the housing specifically. Weep hole 249 may be located away from the crystals of the transducer, or opposite the slot, to avoid any interference or attenuation of the image.

As best seen in FIG. 16C, catheter 2 may be provided with guidewire lumen 250 distal of housing 222. Two ribs 234 may be located directly opposite slot 223. These two ribs 234 provide a channel or pocket which aligns with the guidewire lumen 250. The guidewire may reside within this channel or pocket. This structure provides at least two functions. First, it minimizes the crossing profile of the guidewire GW over the housing since the guidewire is maintained between the ribs. Second, confining the guidewire to a location between the ribs which is opposite the slot reduces both the artifacts in the image and attenuation of the signal which may be caused if the guidewire is positioned at or near the slot. This positioning, in addition to minimizing the distance between the outer diameter of the housing and the guidewire, prevents significant ringing or distortion of the image and thus improves the overall quality of the image produced. Software may further be used to filter and remove any ringing or residual artifacts produced by the guidewire GW.

FIGS. 18A to 18D illustrate an alternate embodiment of the housing of catheter 2 in which transducer 40 is housed within housing 222a. The outer wall of housing 222a may have a thickness which serves to minimize acoustic attenuation by allowing better penetration of the acoustic ultrasound signal produced by the transducer. However, in order to preserve the structural integrity of housing 222a the housing may be provided with ribs as previously described, or may have an increased wall thickness. Transducer 40 will produce a 360° image through the outer wall of housing 222a and slots 223a, with the radial angled portion of the 360° imaged vessel obtained through slots 223a being of a higher quality than the remainder of the radial angled portion of the 360° imaged vessel obtained through the outer wall of housing 222a. Slots 223a may produce substantially identical or differing radial angles of the imaged vessel in the range of 60° to 180° of the circumference of the vessel and may be more specifically in the range of 65° to 85° and further may be 73°. Slots 223a may have longitudinal widths of 0.051 inches and transverse or radial widths of 0.041 inches. It should be understood that slots 223a of housing 222a could have any desired dimensions depending upon the application. It has been found that some signal distortion may be caused if the slots 223a (or other slots described in connection with other embodiments) have sharp edges or corners. Therefore, to minimize any effect of distortion and to minimize the amount or size of any artifacts in the image, the edges of the opening of slots 223a may be shaped or angled to coincide with the radius of the catheter.

FIGS. 19A to 19D illustrate a further alternate embodiment of a transducer housing 222b. Housing 222b is similar to housing 222 except that is does not have ribs 234. Housing 222b includes opening 223b, and pin holes 260b, which correspond in structure and function to opening 223, and pin holes 260 of housing 222. Thus, those elements need not be described further in connection with housing 222b. Housing 222b may have a smaller diameter or crossing profile than housing 222.

Figure 20:
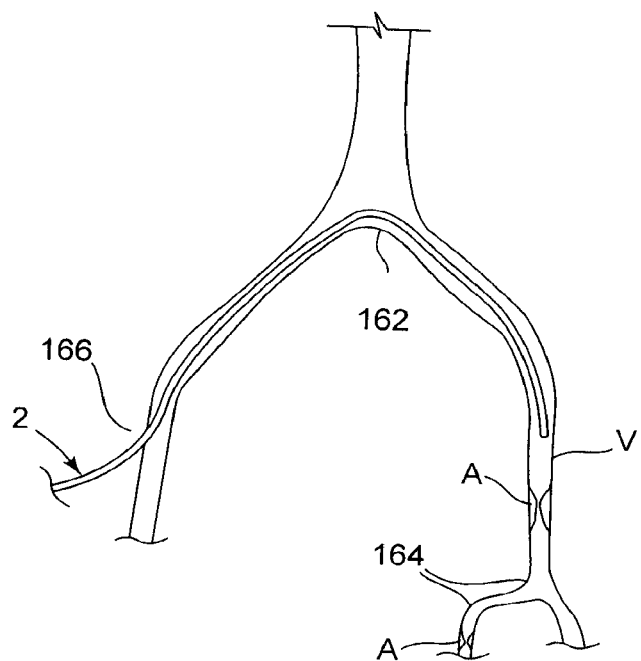
FIG. 20 is a schematic view of an atherectomy catheter during use in a body lumen.

Some exemplary methods of the present invention will now be described. One method of the present invention comprises delivering a catheter to a target site in a body lumen. As shown in FIG. 20 catheter 2 can be introduced at an introduction site 166, through a guide catheter or sheath and over a conventional or imaging guidewire using conventional interventional techniques. The debulking catheter can be advanced over the guidewire and out of the guide catheter to the diseased area. The catheter is advanced to the treatment site with the cutter in the stored position as shown in FIG. 6. As shown in FIG. 3 catheter 2 will typically have at least one flexible joint to allow pivoting about one or more axes of rotation to enhance the delivery of the catheter into the tortuous anatomy without dislodging the guide catheter or other sheath.

During catheter 2 advancement over arch 162 or through tortuous bends 164 significant catheter flexibility will be helpful or necessary. When the region of catheter 2 comprised of imaging transducer 40 bends transverse to longitudinal axis LA the transducer mounting configurations of, for example, FIGS. 6, 7, 8A, 8B, 9A, 9B, 10B, 10C, 10D, 10E, 10F, and 15 allow gap G, 127 to be reduced and/or enlarged thereby decoupling the bending stiffness of transducer 40 from catheter body 8 and reducing the force needed to advance catheter 2 around bends 162, 164. In some embodiments the transducer mounting configurations described herein make it possible to advance catheter 2 across bends such as bends 162, 164. Further, as in the embodiments of FIGS. 16A to 19D, the housing and its connection to the proximal catheter body torque shaft may create a longitudinal length of rigidity in the area where the urge force exists in other embodiments of the present application. This length of rigidity may counteract the urge force which is necessary for catheter advancement around bends in lumens of vessels. In order to compensate for this length of increased rigidity it may be necessary to adjust the degree of bend in the catheter body. Further, it may be necessary to adjust and vary the radii of the catheter body proximal to the housing to displace the location of the urge of the catheter to an alternate location in order to maintain the urge force necessary for the distal advancement and proximal retraction of the catheter through the bends of the vessel lumen.

After crossing arch 162, bends 164, and/or other tortuosity the cutter 4 of catheter 2 can be positioned proximal of the treatment site such as atheroma A. Optionally, transducer 40 can be activated and IVUS or other imaging modality can be used to verify the position of the cutter relative to material, for example atheroma, in the vessel V while imaging catheter 2 may be advanced and withdrawn past atheroma A until a treatment strategy is chosen.

Once the position of the catheter is confirmed, the cutter will be retracted proximally and moved out of cutting window to its exposed position. In some embodiments, movement of the cutter can deflect the distal portion of the catheter to increase the profile of the catheter at the target site. Movement of the cutter is typically caused by proximal movement of lever 13 and tensioning of drive shaft 20. When the cutter is moved proximally it contacts ramp or cam surfaces so as to guide the cutter up and at least partially out of the cutting window. Additionally, the distal portion of catheter body rotates about the joint to provide an urging force for the cutter (and catheter body) to move toward the diseased area.

The cutter can be rotated and vessel V can be debulked with the exposed cutter by advancing catheter 2 distally through vessel V. In some embodiments the transducer housing 122 window pattern is used as a guide to assure that cutter 4 is aligned with atheroma A. Preferably, a distal portion of the catheter is rotated around longitudinal axis LA, or pivoted or deflected to position the cutter adjacent the target material. Thereafter, the catheter and the rotating cutter can be moved through the body lumen to remove the target material from the body lumen until imaging indicates that sufficient or all atheroma has been removed by the cutter.

In some embodiments, catheter 2 can be advanced through the vessel V with the cutting element in the stored position to adjacently align slot 223 with the treatment site for imaging. The catheter can then be proximally retracted a distance and the cutting element moved to the working position exposing the cutter. Catheter 2 can then be distally re-advanced to debulk the treatment site with the cutter. The transducer, which can be located directly proximal of the cutter, images the treatment site as the cutter debulks the vessel. After debulking, the cutting element can be moved to a non-working or stored position and the catheter may be advanced or retracted over the treatment site, as desired, while imaging to verify sufficient atheroma has been removed by the cutter. It is to be understood that any or all these steps may be employed by the physician using the catheter and should be noted that in some applications imaging the treatment site before debulking may not be necessary. It should also be noted that any or all of these steps may be performed with any of the catheter embodiments disclosed herein.

After the vessel has been treated sufficiently with catheter 2 the catheter is withdrawn through arch 162, bends 164, and/or other tortuosity, during which significant catheter flexibility will be helpful or necessary. The transducer mourning configurations of, for example, FIGS. 6, 7, 8A, 8B, 9A, 9B, 10B, 10C, 10D, 10E, 10F, and 15 allow gap G, 117 to be reduced and or enlarged thereby decoupling the bending stiffness of transducer 40 from catheter body 8 and reducing the force needed to withdraw catheter 2 around bends 162, 164.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. A catheter for deployment in a vessel comprising:
   a control handle;
   an elongate proximal segment having proximal and distal ends, the proximal end being connected to the control handle;
   a distal tip assembly having proximal and distal ends;
   a tissue-removing element in the distal tip assembly;
   a housing having a proximal end portion comprising a first material, a distal end portion comprising a second material, and a body portion extending between the proximal and distal end portions, the body portion comprising a third material, the first and second materials being different from the third material, the proximal end portion being connected to the distal end of the elongate proximal segment, the distal end portion being connected to the proximal end of the distal tip assembly, the housing having a luminal wall with an inner surface defining a lumen, the luminal wall having at least one slot; and
   a transducer mounted at least partially within the lumen of the housing.

2. The catheter of claim 1 wherein an outer surface of the housing has at least one longitudinally extending rib on the outer surface of the luminal wall.

3. The catheter of claim 2 wherein the at least one longitudinally extending rib on the outer surface of the luminal wall is in the range of 5 to 8 ribs.

4. The catheter of claim 1 wherein the at least one slot in the luminal wall is two slots.

5. The catheter of claim 1 wherein the transducer is at a position spaced from the luminal wall to form a gap between the transducer and the luminal wall.

6. The catheter of claim 1 wherein the transducer is configured to have 360° image capability of the vessel through the luminal wall of the housing and through the at least one slot of the housing, a radial angle of the circumference of the housing imaged by the transducer through the at least one slot in the luminal wall of the housing is in the range of 60° to 180°.

7. The catheter of claim 6 wherein the radial angle is in the range of 120° to 150°.

8. The catheter of claim 7 wherein the radial angle is 130°.

9. The catheter of claim 4 wherein the transducer is configured to have 360° image capability of the vessel through the luminal wall of the housing and through the at least one slot of the housing, radial angle of the circumference of the housing imaged by the transducer through each slot in the luminal wall of the housing is in the range of 60° to 180°.

10. The catheter of claim 9 wherein the radial angle is in the range of 65° to 90°.

11. The catheter of claim 10 wherein the radial angle is 73°.

12. The catheter of claim 1 wherein the first and second materials comprise metal and the third material comprises polymer.

13. The catheter of claim 12 wherein the first material comprises stainless steel, the second material comprises tungsten and the third material comprises acrylonitrile butadiene styrene (ABS).

14. The catheter of claim 12 wherein the distal end of the elongate proximal segment connected to the proximal end portion of the housing comprises stainless steel.

15. The catheter of claim 1 further comprising: a first tubular member having proximal and distal ends and a wall defining a lumen, at least a portion of the first tubular member being positioned within the lumen of the housing and being connected to the proximal end portion of the housing.

16. The catheter of claim 15 wherein a proximal portion of the first tubular member extends proximally from the proximal end of the housing within a lumen in the elongate proximal segment such that the proximal end of the first tubular member is proximal of the distal end of the elongate proximal segment.

17. The catheter of claim 15 further comprising: a second tubular member having proximal and distal ends and a wall defining a lumen, at least a portion of the second tubular member being positioned within the lumen of the first tubular member, a distance between an outer surface of the wall of the second tubular member and an inner surface of the wall of the first tubular member defining a gap between the first and second tubular members; and wherein the transducer further comprises wires extending proximally to the control handle, the wires being positioned to extend through the gap between the first and second tubular members.

18. The catheter of claim 15 wherein the distal end of the first tubular member is proximal of the slot in the housing.

19. The catheter of claim 17 wherein the distal end of the second tubular member is positioned between the distal and proximal ends of the first tubular member and the proximal end of the second tubular member is positioned proximal of the proximal end of the first tubular member.

20. The catheter of claim 1 wherein the distal end of the elongate proximal segment is connected to the proximal end portion of the housing by a weld.

21. The catheter of claim 1 wherein the distal end portion of the housing includes opposing pin holes which are positioned to align with opposing pin holes in the distal tip assembly and wherein the catheter further comprises pins positioned in the aligned pin holes.

22. The catheter of claim 17 further comprising a potting material contained within the gap between the first and second tubular members.

23. A catheter for deployment in a vessel comprising:
a control handle;
an elongate proximal segment having proximal and distal ends, the proximal end being connected to the control handle;
a distal tip assembly having proximal and distal ends;
a tissue-removing element in the distal tip assembly;
a housing having a proximal end portion, a distal end portion, and a body portion extending between the proximal and distal end portions, the proximal end portion being connected to the distal end of the elongate proximal segment, the distal end portion being connected to the proximal end of the distal tip assembly, the housing having at least one slot;
a first tubular member having proximal and distal ends and a wall defining a lumen, at least a portion of the first tubular member being positioned within the lumen of the housing and being connected to the proximal end portion of the housing; and
a transducer mounted at least partially within the lumen of the housing, at least a portion of the transducer being positioned within the lumen of the first tubular member, the transducer having image capability of the vessel through the at least one slot of the housing, the transducer including wires extending proximally to the control handle.

24. The catheter of claim 23 wherein a proximal portion of the first tubular member extends proximally from the proximal end of the housing within a lumen in the elongate proximal segment such that the proximal end of the first tubular member is proximal of the distal end of the elongate proximal segment.

25. The catheter of claim 23 further comprising:
a second tubular member having proximal and distal ends and a wall defining a lumen, at least a portion of the second tubular member being positioned within the lumen of the first tubular member, a distance between an outer surface of the wall of the second tubular member and an inner surface of the wall of the first tubular member defining a gap between the first and second tubular members, the wires extending through the gap between the first and second tubular members.

26. The catheter of claim 23 wherein the distal end of the first tubular member is proximal of the slot in the housing.

27. The catheter of claim 25 wherein the distal end of the second tubular member is positioned between the distal and proximal ends of the first tubular member and the proximal end of the second tubular member is positioned proximal of the proximal end of the first tubular member.

28. The catheter of claim 25 further comprising a potting material contained within the gap between the first and second tubular members.

* * * * *